(12) United States Patent
Shen et al.

(10) Patent No.: US 10,662,198 B2
(45) Date of Patent: May 26, 2020

(54) POLYMORPHIC FORM OF COMPOUND, PREPARATION METHOD AND USE THEREOF

(71) Applicant: QILU PHARMACEUTICAL CO., LTD., Jinan, Shandong (CN)

(72) Inventors: Jianwei Shen, Shandong (CN); Jin Zhang, Shandong (CN); Long Li, Shandong (CN); Yonghong Gao, Shandong (CN); Zhantao Zhang, Shandong (CN); Yong Zhang, Shandong (CN)

(73) Assignee: QILU PHARMACEUTICAL CO., LTD., Jinan, Shandong (CN)

( * ) Notice: Subject to any disclaimer, the term of this patent is extended or adjusted under 35 U.S.C. 154(b) by 0 days.

(21) Appl. No.: 16/606,144

(22) PCT Filed: Apr. 26, 2018

(86) PCT No.: PCT/CN2018/084608
§ 371 (c)(1),
(2) Date: Oct. 17, 2019

(87) PCT Pub. No.: WO2018/196805
PCT Pub. Date: Nov. 1, 2018

(65) Prior Publication Data
US 2020/0039992 A1 Feb. 6, 2020

(30) Foreign Application Priority Data

Apr. 28, 2017 (CN) .......................... 2017 1 0295287

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................. C07D 487/04
See application file for complete search history.

(56) References Cited

FOREIGN PATENT DOCUMENTS

| WO | 2015180631 A1 | 12/2015 |
| WO | 2017076286 A1 | 5/2017 |

OTHER PUBLICATIONS

Hans Jorg Hacker et al., "Antivirals interacting with hepatitis B virus core protein and core mutations may misdirect capsid assembly in a similar fashion", Biochemical Pharmacology, 66 (2003), pp. 2273-2279.
Karl Deres et al., "Inhibition of Hepatitis B Virus Replication by Drug-Induced Depletion of Nucleocapsids", Science, vol. 299, Feb. 7, 2003, pp. 893-896.

*Primary Examiner* — Paul V Ward
(74) *Attorney, Agent, or Firm* — Novick, Kim & Lee, PLLC; Allen Xue

(57) ABSTRACT

The present disclosure relates to polymorphic forms of the compound methyl (3R,6S)-6-amino-sulfonylamino-1-(thiazol-2-yl)-3-(2,3,4-trifluorophenyl)-3,5,6,7-tetrahydropyrrolo[1,2-c]pyrimidin-4-formate (compound 1). The present disclosure further relates to a pharmaceutical composition and pharmaceutical use and a preparation method of the polymorphic forms of compound 1.

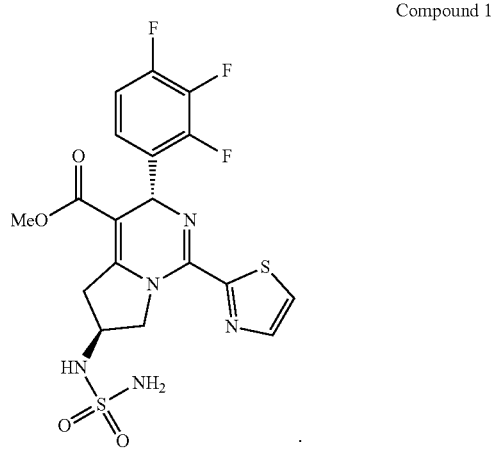

Compound 1

20 Claims, 14 Drawing Sheets

POLYMORPHIC FORM OF COMPOUND, PREPARATION METHOD AND USE THEREOF

CROSS-REFERENCE TO RELATED APPLICATIONS

This application is a national entry of International Application No. PCT/CN2018/084608 filed on Apr. 26, 2018, which claims the benefit of priority from Chinese patent application No. 201710295287.9, filed on Apr. 28, 2017, entitled "POLYMORPHIC FORM OF COMPOUND, PREPARATION METHOD AND USE THEREOF," the entire contents of which are incorporated herein by reference in their entirety.

TECHNICAL FIELD

The present disclosure belongs to the field of pharmaceutical crystalline forms, and particularly relates to polymorphic forms of compounds, preparation methods and uses thereof, in particular to the polymorphic forms of methyl (3R,6S)-6-aminosulfonyl-amino-1-(thiazol-2-yl)-3-(2,3,4-trifluorophenyl)-3,5,6,7-tetrahydropyrrolo[1,2-c]pyrimidin-4-formate, preparation methods and uses thereof.

BACKGROUND ART

Hepatitis B virus, which can cause acute and/or persistent/progressive chronic diseases, belongs to the family of hepatic viruses. Hepatitis B virus can also cause many other clinical manifestations in pathological morphology, especially chronic inflammation of the liver, cirrhosis of the liver, and carcinogenesis of hepatocytes. In addition, its co-infection with hepatitis D leads to an adverse effect during the development of the disease.

Conventional agents that are approved for the treatment of chronic hepatitis are interferon and lamivudine. However, interferon has only moderate activity but high toxic side effects; although lamivudine has good activity, its drug resistance increases rapidly during the treatment and the rebound effect often occurs after stopping treatment. Lamivudine (3-TC) has an $IC_{50}$ value of 300 nM (Science, 299 (2003), 893-896).

Deres et al. reports dihydropyrimidine (HAP) compounds substituted by a heteroaryl ring, represented by Bay41-4109 and Bay39-5493, which are capable of inhibiting HBV replication by preventing the formation of normal nucleocapsids. Bay41-4109 exhibited good drug metabolism parameters in clinical studies (Science, 299 (2003), 893-896). Studies on its mechanism of action revealed that dihydropyrimidine compounds substituted by a heteroaryl ring change the angle between the dimers forming the nucleocapsid by acting on the 113-143 amino acid residues of the core protein, resulting in the formation of unstable expanded nucleocapsid and the acceleration of core protein degradation (Biochem. Pharmacol., 66 (2003), 2273-2279). In addition, the patent application WO2015180631 also discloses compounds as HBV inhibitors. Currently, there is still a need to develop new compounds which can be effectively used as antiviral drugs, especially drugs for the treatment and/or prevention of hepatitis B and especially drug crystalline forms with improved stability, hygroscopicity and efficacy, which are more suitable for forming drugs, thereby achieving good effects in the pharmaceutical manufacturing and drug application stages.

SUMMARY

In order to improve the problems in the prior art, an embodiment of the present disclosure provides a polymorphic form of methyl (3R,6S)-6-aminosulfonylamino-1-(thiazol-2-yl)-3-(2,3,4-trifluorophenyl)-3,5,6,7-tetrahydropyrrolo[1,2-c]pyrimidin-4-formate:

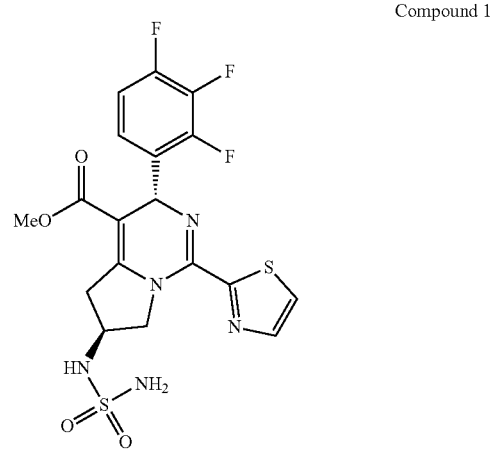 [SMILES: COC(=O)C1=C2C[C@H](NS(N)(=O)=O)CN2C(c2nccs2)=N[C@H]1c1ccc(F)c(F)c1F]

Compound 1

An embodiment of the present disclosure provides a crystalline form II of a hemihydrate of the compound 1, which is characterized by an X-ray powder diffraction pattern having characteristic peaks at 2θ angles of 4.15±0.20°, 4.99±0.20°, 8.78±0.20°, 9.44±0.20°, 18.47±0.20°, and 18.93±0.20° using Cu-Kα radiation.

Preferably, the crystalline form II is characterized by an X-ray powder diffraction pattern having characteristic peaks at 2θ angles of 4.15±0.20°, 4.99±0.20°, 7.33±0.20°, 8.78±0.20°, 9.44±0.20°, 10.00±0.20°, 18.47±0.20°, 18.93±0.20° using Cu-Kα radiation.

Preferably, the crystalline form II is characterized by an X-ray powder diffraction pattern having characteristic peaks at 2θ angles of 4.15±0.20°, 4.99±0.20°, 7.33±0.20°, 7.88±0.20°, 8.78±0.20°, 9.44+0.20°, 10.01±0.20°, 10.96±0.20°, 11.61±0.20°, 12.54±0.20°, 14.18±0.20°, 16.65±0.20°, 17.49±0.20°, 18.47±0.20°, 18.93±0.20°, 19.62±0.20°, 20.13±0.20°, 21.49±0.20°, 22.08±0.20°, 22.51±0.20°, 23.59±0.20°, 24.68±0.20°, 25.37±0.20°, 26.56±0.20°, 27.24±0.20°, 27.76±0.20°, 28.56±0.20°, 30.02±0.20°, 32.18±0.20° using Cu-Kα radiation.

Preferably, the crystalline form II is characterized by an X-ray powder diffraction pattern having characteristic peaks at 2θ angles as shown in Table 1, with the error range at +0.20° using Cu-Kα radiation:

TABLE 1

XRPD analytical data of the crystalline form II of compound 1

| Peak Number | 2θ | I % |
|---|---|---|
| 1 | 4.15 | 96.88 |
| 2 | 4.99 | 94.08 |
| 3 | 7.33 | 41.00 |
| 4 | 7.88 | 33.48 |
| 5 | 8.78 | 55.40 |
| 6 | 9.44 | 67.28 |
| 7 | 10.01 | 42.39 |
| 8 | 10.96 | 14.95 |

TABLE 1-continued

XRPD analytical data of the
crystalline form II of compound 1

| Peak Number | 2θ | I % |
|---|---|---|
| 9 | 11.61 | 33.98 |
| 10 | 12.54 | 20.40 |
| 11 | 14.18 | 17.21 |
| 12 | 16.65 | 51.71 |
| 13 | 17.49 | 11.49 |
| 14 | 18.47 | 100.00 |
| 15 | 18.93 | 60.83 |
| 16 | 19.62 | 29.84 |
| 17 | 20.13 | 6.81 |
| 18 | 21.49 | 9.40 |
| 19 | 22.08 | 21.79 |
| 20 | 22.51 | 21.20 |
| 21 | 23.59 | 11.90 |
| 22 | 24.68 | 16.88 |
| 23 | 25.37 | 21.99 |
| 24 | 26.56 | 18.52 |
| 25 | 27.24 | 5.52 |
| 26 | 27.76 | 5.96 |
| 27 | 28.56 | 11.16 |
| 28 | 30.02 | 7.45 |
| 29 | 32.18 | 2.83. |

Preferably, the crystalline form II of the compound has a powder X-ray diffraction pattern substantially as shown in FIG. 1.

According to an embodiment of the present disclosure, a differential scanning calorimetry (DSC) analysis of the crystalline form II exhibits a first endothermic peak when heated to a peak temperature at about 103° C., an exothermic peak when heated to a peak temperature at about 149° C. and a second exothermic peak when heated to a peak temperature at about 176° C.

According to an embodiment of the present disclosure, a thermogravimetric analysis (TGA) of the crystalline form II has a weight loss of about 1.8% when heated to 120° C.

Preferably, the crystalline form II has a DSC-TGA pattern substantially as shown in FIG. 2.

Preferably, the crystalline form II has a scanning electron micrograph substantially as shown in FIG. 3.

According to an embodiment of the present disclosure, the purity of the crystalline form II may be 95% or more, preferably 99% or more, for example, 99.3% or 99.6%.

An embodiment of the present disclosure provides a crystalline form IV of a monohydrate of the compound 1, which is characterized by an X-ray powder diffraction pattern having characteristic peaks at 2θ angles of 5.04±0.20°, 7.20±0.20°, 7.68±0.20°, 9.81±0.20°, 10.08±0.20°, 14.43±0.20° using Cu-Kα radiation.

Preferably, the crystalline form IV is characterized by an X-ray powder diffraction pattern having characteristic peaks at 2θ angles of 5.04±0.20°, 7.20±0.20°, 7.68±0.20°, 9.35±0.20°, 9.81±0.20°, 10.08±0.20°, 14.43±0.20, 18.07±0.20° using Cu-Kα radiation.

Preferably, the crystalline form IV is characterized by an X-ray powder diffraction pattern having characteristic peaks at 2θ angles of 5.04±0.20°, 6.54±0.20°, 7.20±0.20°, 7.68±0.20°, 8.13±0.20°, 9.35±0.20°, 9.81±0.20°, 10.08±0.20°, 10.71±0.20°, 13.33±0.20°, 14.43±0.20°, 15.15±0.20°, 15.42±0.20°, 16.39±0.20°, 18.07±0.20°, 18.42±0.20°, 18.80±0.20°, 19.00±0.20°, 19.71±0.20°, 20.34±0.20°, 21.72±0.20°, 22.29±0.20°, 23.62±0.20°, 24.14±0.20°, 24.52±0.20°, 25.39±0.20°, 25.79±0.20°, 26.37±0.20°, 27.89±0.20°, 29.09±0.20°, 31.18±0.20°, 32.51±0.20°, 34.73±0.20° using Cu-Kα radiation.

Preferably, the crystalline form IV is characterized by an X-ray powder diffraction pattern having characteristic peaks at 2θ angles as shown in Table 2, with the error range at ±0.20° using Cu-Kα radiation:

TABLE 2

XRPD analytical data of the
crystalline form IV of compound 1

| Peak Number | 2θ | I % |
|---|---|---|
| 1 | 5.04 | 100.00 |
| 2 | 6.54 | 15.47 |
| 3 | 7.20 | 79.38 |
| 4 | 7.68 | 50.94 |
| 5 | 8.13 | 20.30 |
| 6 | 9.35 | 30.62 |
| 7 | 9.81 | 40.57 |
| 8 | 10.08 | 32.75 |
| 9 | 10.71 | 2.93 |
| 10 | 13.33 | 5.75 |
| 11 | 14.43 | 59.51 |
| 12 | 15.15 | 19.41 |
| 13 | 15.42 | 31.53 |
| 14 | 16.39 | 15.66 |
| 15 | 18.07 | 32.95 |
| 16 | 18.42 | 30.80 |
| 17 | 18.80 | 14.23 |
| 18 | 19.00 | 16.10 |
| 19 | 19.71 | 19.62 |
| 20 | 20.34 | 29.85 |
| 21 | 21.72 | 13.67 |
| 22 | 22.29 | 4.40 |
| 23 | 23.62 | 4.08 |
| 24 | 24.14 | 6.82 |
| 25 | 24.52 | 11.27 |
| 26 | 25.39 | 11.75 |
| 27 | 25.79 | 5.32 |
| 28 | 26.37 | 21.34 |
| 29 | 27.89 | 3.18 |
| 30 | 29.09 | 6.89 |
| 31 | 31.18 | 8.74 |
| 32 | 32.51 | 2.99 |
| 33 | 34.73 | 2.28. |

Preferably, the crystalline form IV has a powder X-ray diffraction pattern substantially as shown in FIG. 4.

According to an embodiment of the present disclosure, a differential scanning calorimetry (DSC) analysis of the crystalline form IV exhibits a first endothermic peak when heated to a peak temperature at about 76.2° C., a second endothermic when heated to a peak temperature at about 115.2° C., a first exothermic peak when heated to a peak temperature at about 156.2° C., and a third endothermic peak when heated to a peak temperature at about 176.2° C.

Preferably, a thermogravimetric analysis (TGA) of the crystalline form IV has a weight loss of about 3.3% when heated to 112° C.

Preferably, the crystalline form IV has a DSC-TGA pattern substantially as shown in FIG. 5.

Preferably, the crystalline form IV has a scanning electron micrograph substantially as shown in FIG. 6.

Preferably, the purity of the crystalline form IV may be 95% or more, preferably 98% or more, for example, 99.1% or 99.5%.

An embodiment of the present disclosure provides a crystalline form V of a hemihydrate of the compound 1, which is characterized by an X-ray powder diffraction pattern having characteristic peaks at 2θ angles of 6.76±0.20°, 10.20±0.20°, 10.79±0.20°, 17.14±0.20°, 19.26±0.20°, 19.69±0.20°, 20.33±0.20°, 20.83±0.20°, 22.60±0.20°, 23.47±0.20°, 24.73±0.20° using Cu-Kα radiation.

Preferably, the crystalline form V is characterized by an X-ray powder diffraction pattern having characteristic peaks at 2θ angles of 6.76±0.20°, 10.20±0.20°, 10.79±0.20°, 12.13±0.20°, 13.55±0.20°, 14.54±0.20°, 17.14±0.20°, 17.90±0.20°, 18.30±0.20°, 18.96±0.20°, 19.26±0.20°, 19.69±0.20°, 20.33±0.20°, 20.83±0.20°, 21.71±0.20°, 22.29±0.20°, 22.60±0.20°, 23.47±0.20°, 24.73±0.20°, 26.32±0.20°, 27.63±0.20°, 28.32±0.20°, 30.75±0.20°, 32.81±0.20°, 34.10±0.20°, 36.11±0.20°, 38.29±0.20°, 40.31±0.20°, 41.58±0.20°, 43.47±0.20° using Cu-Kα radiation.

Preferably, the crystalline form V is characterized by an X-ray powder diffraction pattern having characteristic peaks at 2θ angles as shown in Table 3, with the error range at +0.20° using Cu-Kα radiation:

TABLE 3

XRPD analytical data of the crystalline form V of compound 1

| Peak Number | 2θ | I % |
|---|---|---|
| 1 | 6.76 | 40.73 |
| 2 | 10.20 | 51.22 |
| 3 | 10.79 | 81.35 |
| 4 | 12.13 | 10.67 |
| 5 | 13.55 | 36.86 |
| 6 | 14.54 | 29.00 |
| 7 | 17.14 | 100.00 |
| 8 | 17.90 | 10.09 |
| 9 | 18.30 | 17.58 |
| 10 | 18.96 | 31.26 |
| 11 | 19.26 | 41.75 |
| 12 | 19.69 | 50.25 |
| 13 | 20.33 | 42.45 |
| 14 | 20.83 | 74.39 |
| 15 | 21.71 | 17.61 |
| 16 | 22.29 | 22.66 |
| 17 | 22.60 | 40.52 |
| 18 | 23.47 | 83.08 |
| 19 | 24.73 | 91.58 |
| 20 | 26.32 | 26.16 |
| 21 | 27.63 | 4.22 |
| 22 | 28.32 | 8.49 |
| 23 | 30.75 | 10.55 |
| 24 | 32.81 | 7.51 |
| 25 | 34.10 | 5.20 |
| 26 | 36.11 | 7.68 |
| 27 | 38.29 | 4.81 |
| 28 | 40.31 | 3.86 |
| 29 | 41.58 | 2.49 |
| 30 | 43.47 | 3.18. |

Preferably, the crystalline form V has a powder X-ray diffraction pattern substantially as shown in FIG. 7.

According to an embodiment of the present disclosure, a differential scanning calorimetry (DSC) analysis of the crystalline form V exhibits a first endothermic peak when heated to a peak temperature at about 94.6° C., and a second endothermic peak when heated to a peak temperature at about 169.0° C.

According to an embodiment of the present disclosure, a thermogravimetric analysis (TGA) of the crystalline form V has a weight loss of about 1.8% when heated to 127° C.

Preferably, the crystalline form V has a DSC-TGA pattern substantially as shown in FIG. 8.

Preferably, the purity of the crystalline form V may be 95% or more, preferably 98% or more, for example, 99.1% or 99.4%.

An embodiment of the present disclosure provides a crystalline form VI of a 1,4-dioxane solvate of the compound 1, which is characterized by an X-ray powder diffraction pattern having characteristic peaks at 2θ angles of 7.82±0.20°, 17.55±0.20°, 19.89±0.20°, 25.48±0.20° using Cu-Kα radiation.

Preferably, the crystalline form VI is characterized by an X-ray powder diffraction pattern having characteristic peaks at 2θ angles of 5.57±0.20°, 7.82±0.20°, 12.30±0.20°, 17.55±0.20°, 18.34±0.20°, 19.15±0.20°, 19.89±0.20°, 24.46±0.20°, 25.48±0.20° using Cu-Kα radiation.

Preferably, the crystalline form VI is characterized by an X-ray powder diffraction pattern having characteristic peaks at 2θ angles of 5.57±0.20°, 7.82±0.20°, 10.97±0.20°, 12.30±0.20°, 15.62±0.20°, 16.66±0.20°, 17.55±0.20°, 17.99±0.20°, 18.34±0.20°, 19.15±0.20°, 19.89±0.20°, 21.08±0.20°, 21.40±0.20°, 22.03±0.20°, 22.70±0.20°, 22.70±0.20°, 22.93±0.20°, 23.48±0.20°, 24.46±0.20°, 24.71±0.20°, 25.48±0.20°, 26.32±0.20°, 27.65±0.20°, 27.98±0.20°, 28.50±0.20°, 29.44±0.20°, 30.05±0.20°, 31.48±0.20°, 32.44±0.20°, 33.77±0.20°, 34.45±0.20°, 35.36±0.20°, 36.08±0.20°, 37.52±0.20°, 38.22±0.20°, 39.20±0.20°, 39.83±0.20°, 40.32±0.20°, 41.52±0.20°, 42.51±0.20°, 43.42±0.20° using Cu-Kα radiation.

Preferably, the crystalline form VI is characterized by an X-ray powder diffraction pattern having characteristic peaks at 2θ angles as shown in Table 4, with the error range at +0.20° using Cu-Kα radiation:

TABLE 4

XRPD analytical data of the crystalline form VI of compound 1

| Peak Number | 2θ | I % |
|---|---|---|
| 1 | 5.57 | 17.58 |
| 2 | 7.82 | 100.00 |
| 3 | 10.97 | 4.63 |
| 4 | 12.30 | 35.23 |
| 5 | 15.62 | 13.66 |
| 6 | 16.66 | 14.71 |
| 7 | 17.55 | 62.66 |
| 8 | 17.99 | 4.30 |
| 9 | 18.34 | 15.16 |
| 10 | 19.15 | 27.41 |
| 11 | 19.89 | 59.87 |
| 12 | 21.08 | 10.37 |
| 13 | 21.40 | 3.78 |
| 14 | 22.03 | 9.87 |
| 15 | 22.70 | 7.63 |
| 16 | 22.93 | 12.29 |
| 17 | 23.48 | 5.63 |
| 18 | 24.46 | 20.88 |
| 19 | 24.71 | 9.14 |
| 20 | 25.48 | 40.43 |
| 21 | 26.32 | 2.67 |
| 22 | 27.65 | 4.64 |
| 23 | 27.98 | 4.31 |
| 24 | 28.50 | 1.68 |
| 25 | 29.44 | 7.45 |
| 26 | 30.05 | 8.67 |
| 27 | 31.48 | 3.64 |
| 28 | 32.44 | 2.03 |
| 29 | 33.77 | 2.36 |
| 30 | 34.45 | 1.01 |
| 31 | 35.36 | 1.05 |
| 32 | 36.08 | 0.68 |
| 33 | 37.52 | 3.99 |
| 34 | 38.22 | 1.65 |
| 35 | 39.20 | 3.11 |
| 36 | 39.83 | 1.91 |
| 37 | 40.32 | 2.62 |
| 38 | 41.52 | 1.39 |
| 39 | 42.51 | 1.42 |
| 40 | 43.42 | 1.35. |

Preferably, the crystalline form VI has a powder X-ray diffraction pattern substantially as shown in FIG. 9.

According to an embodiment of the present disclosure, a differential scanning calorimetry (DSC) analysis of the crystalline form VI exhibits a first endothermic peak when heated to a peak temperature at about 105.2° C., and a second endothermic peak when heated to a peak temperature at about 152.1° C.

According to an embodiment of the present disclosure, a thermogravimetric analysis (TGA) of the crystalline form VI has a weight loss of about 6.5% when heated to 130° C.

Preferably, the crystalline form VI has a DSC-TGA pattern substantially as shown in FIG. 10.

Preferably, the crystalline form VI has a scanning electron micrograph substantially as shown in FIG. 11.

Preferably, the purity of the crystalline form VI may be 95% or more, preferably 99% or more, for example, 99.5% or 99.7%.

An embodiment of the present disclosure provides a crystalline form VII of an anhydrate of the compound 1, which is characterized by an X-ray powder diffraction pattern having characteristic peaks at 2θ angles of 4.94±0.20°, 7.21±0.20°, 7.65±0.20°, 9.85±0.20°, 20.05±0.20°, 23.95±0.20° using Cu-Kα radiation.

Preferably, the crystalline form VII is characterized by an X-ray powder diffraction pattern having characteristic peaks at 2θ angles of 4.94±0.20°, 7.21±0.20°, 7.65±0.20°, 8.01±0.20°, 9.85±0.20°, 14.54±0.20°, 20.05±0.20°, 23.95±0.20° using Cu-Kα radiation.

Preferably, the crystalline form VII is characterized by an X-ray powder diffraction pattern having characteristic peaks at 2θ angles of 4.94±0.20°, 7.21±0.20°, 7.65±0.20°, 8.01±0.20°, 9.85±0.20°, 14.54±0.20°, 16.21±0.20°, 17.64±0.20°, 18.28±0.20°, 18.65±0.20°, 20.05±0.20°, 22.59±0.20°, 23.95±0.20° using Cu-Kα radiation.

Preferably, the crystalline form VII is characterized by an X-ray powder diffraction pattern having characteristic peaks at 2θ angles as shown in Table 5, with the error range at ±0.20° using Cu-Kα radiation:

TABLE 5

XRPD analytical data of the crystalline form VII of compound 1

| Peak Number | 2θ | I % |
|---|---|---|
| 1 | 4.94 | 100.00 |
| 2 | 7.21 | 79.61 |
| 3 | 7.65 | 41.08 |
| 4 | 8.01 | 37.30 |
| 5 | 9.85 | 48.40 |
| 6 | 14.54 | 36.34 |
| 7 | 16.21 | 12.54 |
| 8 | 17.64 | 21.16 |
| 9 | 18.28 | 33.56 |
| 10 | 18.65 | 22.62 |
| 11 | 20.05 | 43.29 |
| 12 | 22.59 | 28.47 |

Preferably, the crystalline form VII has a powder X-ray diffraction pattern substantially as shown in FIG. 12.

According to an embodiment of the present disclosure, a differential scanning calorimetry (DSC) analysis of the crystalline form VII shows a first endothermic peak when heated to a peak temperature at about 112.1° C., a first exothermic peak when heated to a peak temperature at about 151.7° C., and a second endothermic peak when heated to a peak temperature of 176.1° C.

According to an embodiment of the present disclosure, a thermogravimetric analysis (TGA) of crystalline form VII has a weight loss of about 0.9% when heated to 95° C.

Preferably, the crystalline form VII of compound 1 has a DSC-TGA pattern substantially as shown in FIG. 13.

Preferably, the crystalline form VII of compound 1 has a scanning electron micrograph substantially as shown in FIG. 14.

Preferably, the purity of the crystalline form VII may be of 98% or more, preferably 99% or more, for example, 99.3% or 99.6%.

An embodiment of the present disclosure provides a process for the preparation of the polymorphic form.

According to an embodiment of the present disclosure, a method of preparing the crystalline form II is provided, comprising the following steps:

mixing the compound 1 with a halogenated alkane solvent and water, heating the mixture to reflux to obtain a clear solution, cooling, and collecting the obtained crystalline form II;

alternatively, an embodiment of the present disclosure also provides a method for preparing the crystalline form II, comprising the following steps:

mixing the compound 1 with a halogenated alkane solvent to obtain a clear solution, adding water, and volatilizing or evaporating the solvent to obtain the crystalline form II.

The halogenated alkane solvent may be selected from one or more of the group consisting of dichloromethane, chloroform, carbon tetrachloride, preferably dichloromethane;

according to an embodiment of the present disclosure, the mass (g)-to-volume (mL) ratio of the compound 1 to the halogenated alkane solvent may be from 1:2 to 1:50, preferably from 1:5 to 1:20, for example from 1:5 to 1:10.

According to an embodiment of the present disclosure, the volume ratio of the halogenated alkane solvent to water may be from 1:1 to 40:1, preferably from 10:1 to 30:1, such as from 20:1 to 30:1; as an illustrative example, dichloromethane and water with a volume ratio of 20:1 are used, or dichloromethane and water with a volume ratio of 26.7:1 are used.

According to an embodiment of the present disclosure, the volatilization can be carried out at a temperature suitable for volatilization or evaporation of the solvent, for example at 10° C.-100° C., for example at 20° C.-60° C., such as 25° C.-40° C.

An embodiment of the present disclosure also provides a preparation method of the crystalline form IV, comprising the following steps:

dissolving the compound 1 in an ether solvent or a nitrile solvent, adding the resulting solution to water and stirring to obtain the crystalline form IV;

wherein, the ether solvent may be selected from one or more of the group consisting of diethyl ether, methyl ethyl ether, methyl tert-butyl ether, dipropyl ether, dibutyl ether, 1,4-dioxane, and tetrahydrofuran, for example, tetrahydrofuran;

the nitrile solvent may be selected from acetonitrile.

According to an embodiment of the present disclosure, the mass (g)-to-volume (mL) ratio of the compound 1 to the ether solvent or the nitrile solvent may be from 1:2 to 1:50, preferably from 1:5 to 1:20, for example from 1:5 to 1:10;

the volume ratio of the ether or nitrile solvent to the water is preferably from 2:1 to 4:1, for example 4:1, as an illustrative example, tetrahydrofuran and water with a volume ratio of 2.5:1 are used, or acetonitrile and water with a volume ratio of 4:1 are used;

the water is preferably purified water;

the stirring can be carried out at 0° C.-40° C., for example 15° C.-35° C., such as 20° C.-25° C.

An embodiment of the present disclosure also provides a preparation method of the crystalline form V, comprising the following steps:

dissolving the compound 1 in a mixed solvent of an ether solvent and an alkane solvent to obtain a suspension, stirring to crystallize to obtain the crystalline form V;

wherein the ether solvent has the definition as described above, preferably 1,4-dioxane; the alkane solvent may be a $C_6$-10 linear or branched alkane, preferably n-heptane; in the mixed solvent of the ether solvent and the alkane solvent, the volume ratio of the ether solvent to the alkane solvent is preferably from 1:1 to 1:4, for example, from 1:3 to 1:4; for example, 1,4-dioxane and n-heptane with a volume ratio of 1:4 or 1:3 are used;

according to an embodiment of the present disclosure, the mass (g)-to-volume (mL) ratio of the compound 1 to the mixed solvent may be from 1:5 to 1:100, preferably from 1:5 to 1:30, for example from 1:5 to 1:10;

the stirring can be carried out at 0° C.-40° C., for example 15° C.-35° C., such as 20° C.-25° C.

An embodiment of the present disclosure also provides a preparation method of the crystalline form VI of the compound 1, which comprises the following steps:

dissolving the compound 1 in a solvent of 1, 4-dioxane to obtain a clear solution, adding an alkane solvent (for example, dropwise) to the clear solution under stirring, and stirring to obtain the crystalline form VI;

wherein the alkane solvent has the definition as described above, and is preferably n-heptane;

according to an embodiment of the present disclosure, the mass (g)-to-volume (mL) ratio of the compound 1 to 1,4-dioxane may be from 1:2 to 1:50, preferably from 1:5 to 1:20, for example, from 1:5 to 1:10;

the volume ratio of the 1,4-dioxane to the alkane solvent is preferably from 1:4 to 1:8, for example, a mixture of 1,4-dioxane and n-heptane with a volume ratio of 1:4, 1:5, 1:6, 1:7 or 1:8 is used;

the stirring can be carried out at 0° C.-60° C., for example 15° C.-55° C., such as 25° C.-50° C.

An embodiment of the present disclosure further provides a method for preparing the crystalline form VII, comprising the following steps:

heating the crystalline form IV of compound 1 as described above and cooling to obtain the crystalline form VII;

preferably, the temperature for heating may be 80° C. or higher, such as 100° C.-150° C.; the time for heating may be 5-50 mins; as an illustrative example, heating and maintaining at 105° C. for 30 mins, or heating at 120° C. for 20 mins;

the heating is preferably carried out under an inert atmosphere, for example under a nitrogen atmosphere;

the temperature for cooling may be from 0° C. to 30° C.

An embodiment of the present disclosure also provides a method for preserving the crystalline form II, wherein the crystalline form II is placed in an environment with a temperature below 60° C., such as 0° C.-40° C.;

preferably, according to the method for preserving the crystalline form II, the relative humidity may be below 92.5% RH, preferably below 80% RH, such as below 60% RH.

An embodiment of the present disclosure also provides a method for preserving the crystalline form IV, wherein the crystalline form IV is placed in an environment with a relative humidity of 92.5% RH or less, such as 0-80% RH.

Preferably, according to the method for preserving the crystalline form IV, wherein the temperature may be below 60° C., for example 0° C.-40° C.

An embodiment of the present disclosure also provides a pharmaceutical composition comprising one or more of the crystalline form II, the crystalline form IV, the crystalline form V, the crystalline form VI or the crystalline form VII of compound 1, and optionally a pharmaceutically acceptable excipient.

An embodiment of the present disclosure also provides a formulation comprising one or more of the crystalline form II, the crystalline form IV, the crystalline form V, the crystalline form VI or the crystalline form VII of compound 1, and optionally a pharmaceutically acceptable excipient.

An embodiment of the present disclosure also provides the use of one or more of the crystalline form II, the crystalline form IV, the crystalline form V, the crystalline form VI or the crystalline form VII of compound 1 as described above in the manufacture of a medicament for the treatment and/or prevention of hepatitis B virus infection.

An embodiment of the present disclosure also provides the use of one or more of the crystalline form II, the crystalline form IV, the crystalline form V, or the crystalline form VII of compound 1 as described above for the treatment and/or prevention of hepatitis B virus infection.

Term Definition and Description

All documents cited in the present disclosure are hereby incorporated by reference in their entirety, and if the meanings expressed by these documents are inconsistent with the present disclosure, the expression of the present disclosure shall prevail. Moreover, even though the various terms and phrases used in the present disclosure have ordinary meanings that are well known to those skilled in the art, the present disclosure is intended to provide a more detailed description and explanation of such terms and phrases. When such terms and phrases are inconsistent with the ordinary meanings, the expression of the present disclosure shall prevail.

The polymorphic forms of compound 1 according to the present disclosure have X-ray powder diffraction characteristic peaks expressed by 2θ angles, wherein "+0.20°" is an allowable measurement error range.

The polymorphic form of compound 1 according to the present disclosure may be used in combination with other active ingredients as long as they don't cause other adverse effects such as allergic reactions.

The term "composition" as used in the present disclosure is meant to include a product comprising a specified amount of each specified ingredient, as well as any product produced directly or indirectly from the combination of specified amounts of specified ingredients.

Those skilled in the art can prepare the polymorphic forms of compound 1 according to the present disclosure into a suitable pharmaceutical composition using known pharmaceutical carriers.

The pharmaceutical composition may be specially formulated for oral administration in solid or liquid form for parenteral injection or rectal administration.

The pharmaceutical composition can be formulated into a variety of dosage forms for ease of administration, for example, oral preparations (such as tablets, capsules, solutions or suspensions); injectable preparations (such as injectable solutions or suspensions or injectable dry powders that can be used immediately after the addition of a drug solvent for injection).

The term "therapeutically and/or prophylactically effective amount" as used in the present disclosure is an amount of a pharmaceutical or pharmaceutical preparation which elicits a biological or medical response of a tissue, system, animal or human which is sought by a researcher, veterinarian, doctor or other person.

When used in the above therapeutic and/or prophylactic uses, the total daily usage of the polymorphic forms and pharmaceutical compositions of compound 1 according to the present disclosure will be determined by the attending physician within the scope of sound medical judgment. The particular therapeutically effective dosage level for any particular patient will depend on a number of factors, including the disorder being treated and the severity of the disorder; the activity of the particular compound employed; the particular composition employed; the age, weight, general health, sex and diet of the patient; the time of administration, the route of administration and the rate of excretion of the particular compound employed; the duration of treatment; the drug used in combination or concurrent with the particular compound employed; and similar factors known in the medical field. For example, it is the practice in the art that the dosage of the compound is started from a level lower than that required to achieve the desired therapeutic effect, and the dosage is gradually increased until the desired effect is obtained.

Advantageous effects according to the present disclosure:

1) The polymorphic forms as prepared according to the present disclosure have good stability, and their purity, color and properties do not change after storage for a long time at room temperature, for example, for 180 days. Moreover, the crystalline forms according to the present disclosure have good fluidity, and are easy to be pulverized and used for preparing a pharmaceutical composition. Finally, the polymorphic forms obtained by according to the present disclosure have high purity and low impurity.

2) The polymorphic forms as prepared according to the present disclosure have good stability and can be stored under high temperature or high humidity conditions. For example, the crystalline form II can be stored under high temperature conditions such as 60° C. for 10 days, with its crystalline form unchanged; the crystalline form IV can be preserved in an environment with a relative humidity of up to 92.5% RH, with its purity, color, and properties unchanged. Accordingly, the polymorphic forms according to the present disclosure have superior stability. 3) The preparation methods of the polymorphic forms according to the present disclosure are simple in process, easy to implement, mild in reaction conditions, and high in product yield. In addition, they do not require multiple purifications, with safe and environmentally friendly operation, which is beneficial to the industrial production of the polymorphic forms.

EXAMPLES

Figure 1:
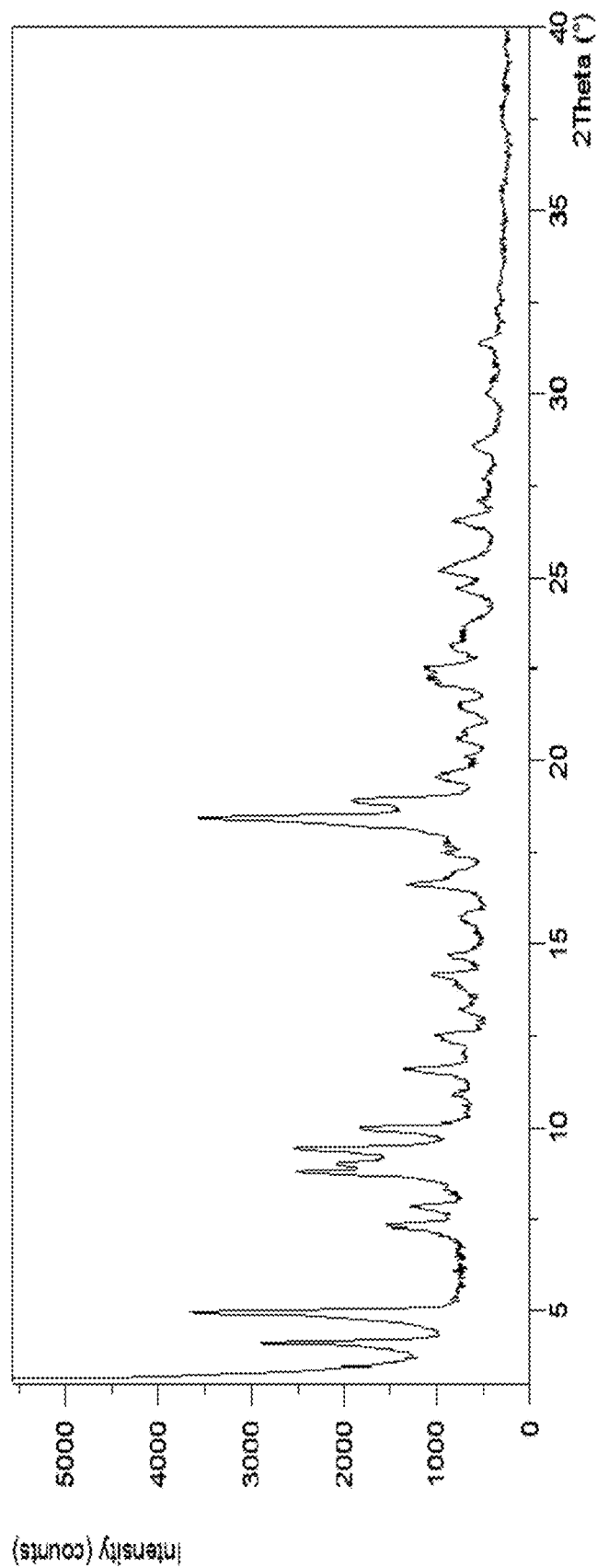
FIG. 1 is an X-ray powder diffraction pattern of the crystalline form II of compound 1.

The polymorphic forms according to the present disclosure, as well as the preparation method thereof and application thereof will be further described in detail below in conjunction with specific examples. The following examples are merely illustrative of the disclosure and are not to be construed as limiting the scope of the present disclosure. The technology that is implemented based on the above-described content of the present disclosure is encompassed within the scope of the present disclosure.

The starting materials and reagents used in the following examples were commercially available or can be prepared by known methods unless otherwise stated.

Test Equipment:

(1) Nuclear magnetic resonance instrument

Instrument model: Varian INOVA-400 NMR instrument.

Test conditions: solvent DMSO-$d_6$.

(2) X-ray powder diffractometer:

Instrument model: PANalytical X-ray powder diffractometer, of which the model number is X'Pert PRO MPD.

Test conditions: the target material is copper, the light pipe is set to (40 Kv 40 mA), the diffraction mode is reflection, the scanning mode is continuous, the divergence slit is ¼°, and the scanning speed is 8°/min.

(3) TGA/DSC1 synchronous thermal analyzer

Instrument model: TGA/DSC1 STAR$^e$ System

Test conditions: the heating rate is 10° C./min, and dry nitrogen is used as the purge gas.

(4) Scanning electron microscope (SEM)

Instrument model: ZEISS Sigma 300.

(5) High performance liquid chromatography

Instrument model: Waters e2695-2489.

Example 1 Preparation of Compound 1

Reaction Route:

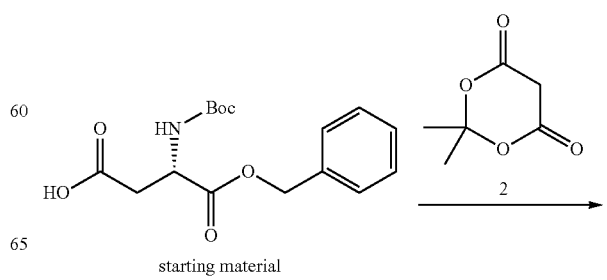

starting material

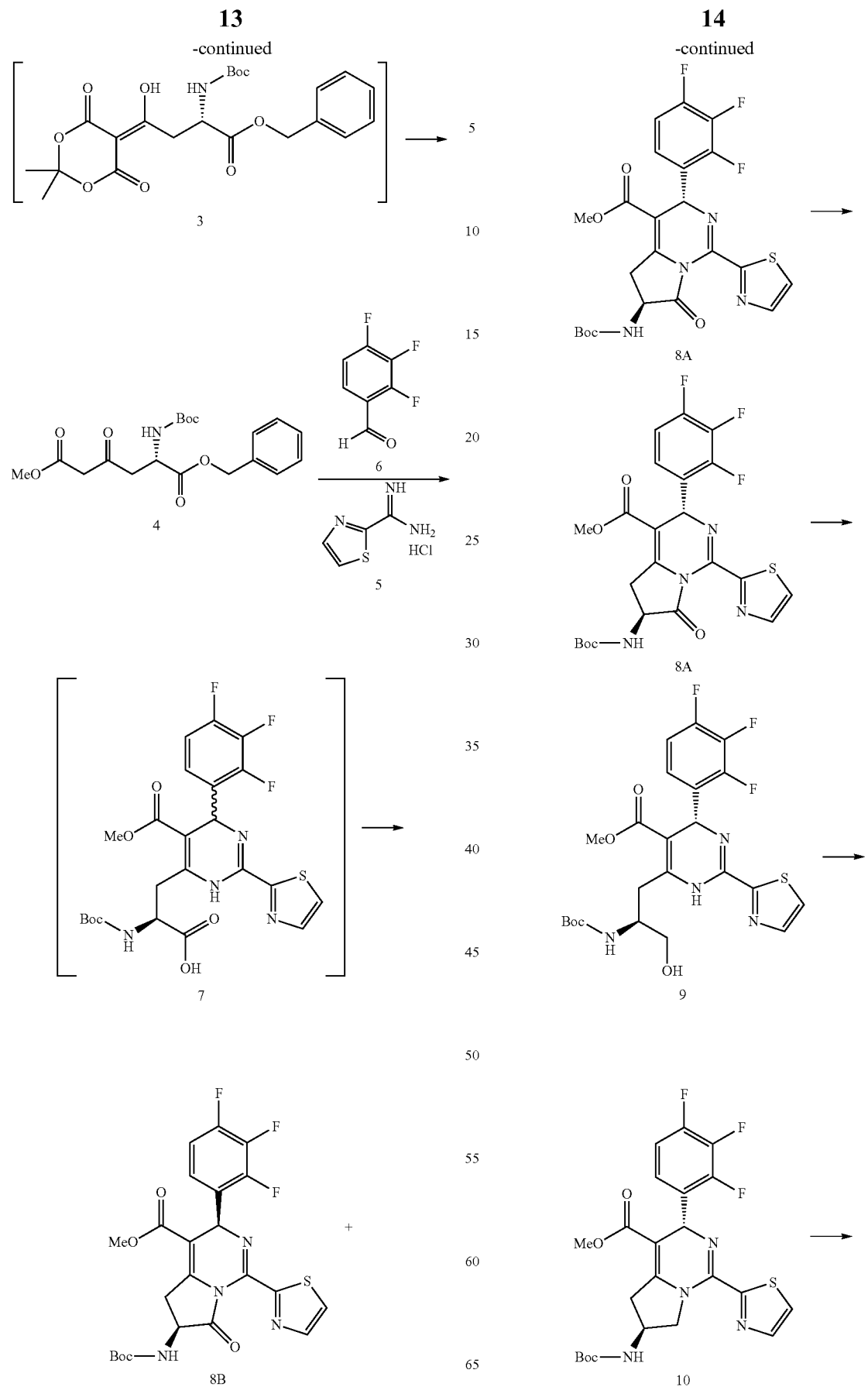

-continued

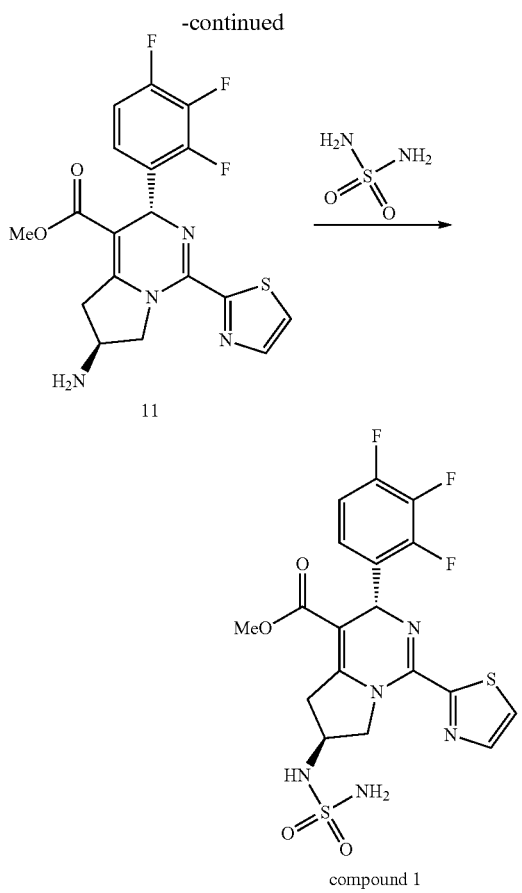

compound 1

Specific Steps:

12 L dichloromethane was added to a 50 L reactor, added with the starting material (5.00 kg, 15.46 mol) followed by addition of 4-N,N-dimethylamino-pyridine (2.83 kg, 23.20 mol) and stirred for 10 minutes. Compound 2 (2.23 kg, 15.46 mol) was added and the temperature was lowered to 0° C. 1-(3-dimethylamino-propyl)-3-ethylcarbodiimide hydrochloride (EDCI) (4.45 kg, 23.20 mol) was dissolved in dichloromethane (20 L) in portions to form a suspension, which was then slowly added dropwise, and the temperature of the feed liquid was maintained lower than 0° C. during the addition. After the addition was completed, stirring was continued for 16 hours. Sampling test was performed by TLC (PE:EtOAc=1:1). After completion of the reaction, the reaction solution was washed with a saturated NaHCO$_3$ solution (20 L*2), subsequently washed once with a saturated NaCl solution (15 L), concentrated under reduced pressure, spun dry, added with 3 L toluene and concentrated under reduced pressure to obtain compound 3, which was separated, with a weight of 6.95 kg, a yield of 87.7%, and a purity of 85%.

Into a 50 L reactor, anhydrous toluene (20 L) was added. Compound 3 (6.95 kg, 15.46 mol) was added. Anhydrous methanol (6.26 L, 154.6 mol) was added under stirring. The internal temperature of the reactor was controlled at 70° C. and the feed liquid was stirred for 16 h. Sampling test was performed by TLC (PE:EtOAc=1:1). After completion of the reaction, the reaction solution was concentrated under reduced pressure to give a red brown viscous liquid. The crude product was dissolved in 6 L EtOH and 10 L petroleum ether. The solution was stirred at 13° C. for 30 minutes with a white solid to be precipitated. After stirring for 2 hours, the solution was allowed to stand overnight and filtered, and the solid was washed three times with petroleum ether (5 L) and then dried to give compound 4 as a product (4.2 kg, 11.07 mol), with a yield of 71.5% and purity of 98%.

Compound 4 (1140 g, 3 mol) and anhydrous THF (7.5 L) were added to a 30 L reaction flask and stirred. Compound 5 (566 g, 3.45 mol), compound 6 (502 g, 1.1 mol) and N-methylmorpholine (760 g, 7.5 mol) were added. The reaction solution was refluxed (60° C.) for 20 hours, cooled to 5° C. to 10° C., added with isobutyl chloroformate (492 g, 3.6 mol, dissolved in 500 mL THF) dropwise, and reacted at 5° C. to 10° C. for 1 hour. After the intermediate carboxylic acid was completely reacted, the reaction was quenched by the addition of water (3 L). Ethyl acetate (9 L) was added for extraction and the organic phase was washed with water (3 L) once, concentrated to give a mother liquor of 2.2 kg. The mother liquid was dissolved in ethyl acetate (3 L), added with tetrahydrofuran (500 mL), slowly added dropwise within-heptane (about 9 L), and stirred at 15° C. overnight to precipitate a solid. The solid was recrystallized from tetrahydrofuran/ethyl acetate/n-heptane solvent system (5 mL/5 mL/10 mL/g) to obtain 500 g compound 8A, of which the purity reached 96%, ee value>96% and yield was 27.1%.

200 mL water was added into a 10 liter reaction flask, added with sodium borohydride (39.2 g, 1.03 mol) to dissolve, and cooled to 0° C. The tetrahydrofuran solution of compound 8A (compound 8A (270.0 g, 0.52 mol) was added with 4.0 L tetrahydrofuran to dissolve for preparing a solution) was slowly added dropwise into an aqueous solution of sodium borohydride for reaction while the temperature was controlled at 0° C. to 5° C. for 3 hours. Sampling test was performed until the reaction was completed. 750 mL hydrochloric acid (1 mol/L) was added to the reaction solution to adjust the pH to 7. The reaction mixture was concentrated to give a crude material, which was extracted with ethyl acetate (500 mL*3) and the organic phases were combined. The organic phase was dried over Na$_2$SO$_4$, filtered to remove the desiccant and evaporated to give 299 g compound 9, with a purity of 97.23% and yield of 96.0%.

Compound 9 (269.0 g, 0.51 mol) was added into a 5 L reactor and dissolved in 1.2 L dichloromethane. Further, 4-N,N-dimethylaminopyridine (187.4 g, 1.53 mol) was added, and the mixture was stirred and cooled to 0° C. A solution of methanesulfonyl chloride (118.09 g, 1.03 mol) in dichloromethane (50 mL) was added dropwise, and after the addition was completed, the mixture was warmed to 30° C.-35° C. and stirred. After the reaction was completed, the pH was adjusted to 2-3 with 1 mol/L of dilute hydrochloric acid. 500 mL water was added to the reaction mixture, and the mixture was extracted with dichloromethane (700 mL*3), and then the organic phases were combined, washed with 1M NaHCO$_3$ (300 mL*2) and dried over anhydrous Na$_2$SO$_4$. After suction filtration, the filtrate was concentrated to give 270 g compound 10 with a yield of 85.7% and purity of 88.56%.

Compound 10 (1.1 kg, 2.1 mol), 9.9 kg ethyl acetate and 0.87 kg concentrated hydrochloric acid were added to a 30 L reactor and stirred for 3 hours. After the reaction was completed, 4.4 kg water was added, and the mixture was separated by extraction. The aqueous phase was washed twice with 6.82 kg dichloromethane, and the liquid phase was further added with 13.25 kg dichloromethane and 1.19 L of methanol, and stirred. After the pH was adjusted to 12-13 with 3 mol/L sodium hydroxide solution, the liquid was separated and the organic phase was collected, and concentrated to dryness under pressure to obtain 0.85 kg compound 11.

Compound 11 (0.082 kg, 0.189 mol, weight content 94.19%), 1,4-dioxane (820 mL), aminosulfonamide (0.189 kg, 0.235 mol) were added to a 30 L reactor successively, with nitrogen displacement. The reaction was carried out under refluxing for 2 hours. After the reaction was completed, the reaction mixture was concentrated to dryness, added with 500 mL dichloromethane, washed with purified water, dried over anhydrous sodium sulfate, and filtered to remove the desiccant, and the filtrate was concentrated under reduced pressure, and then purified by preparative chromatography to give compound 1 with a purity of 97.8%.

$^1$H NMR (400 MHz, DMSO-$d_6$) ppm 3.07 (dd, J=17.69, 6.90 Hz, 1H) 3.48 (dd, J=17.82, 7.53 Hz, 1H) 3.55 (s, 3H) 4.10 (m, J=6.88 Hz, 1H) 4.20 (dd, J=11.29, 6.27 Hz, 1H) 4.51 (dd, J=11.29, 6.78 Hz, 1H) 5.91 (s, 1H) 6.76 (s, 2H) 7.17 (d, J=7.28 Hz, 1H) 7.22-7.29 (m, 2H) 7.89 (d, J=3.26 Hz, 1H) 7.98 (d, J=3.26 Hz, 1H); LCMS: m/z: 488.1 [M+H+].

Example 2 Preparation of the Crystalline Form II of Compound 1

Figure 2:
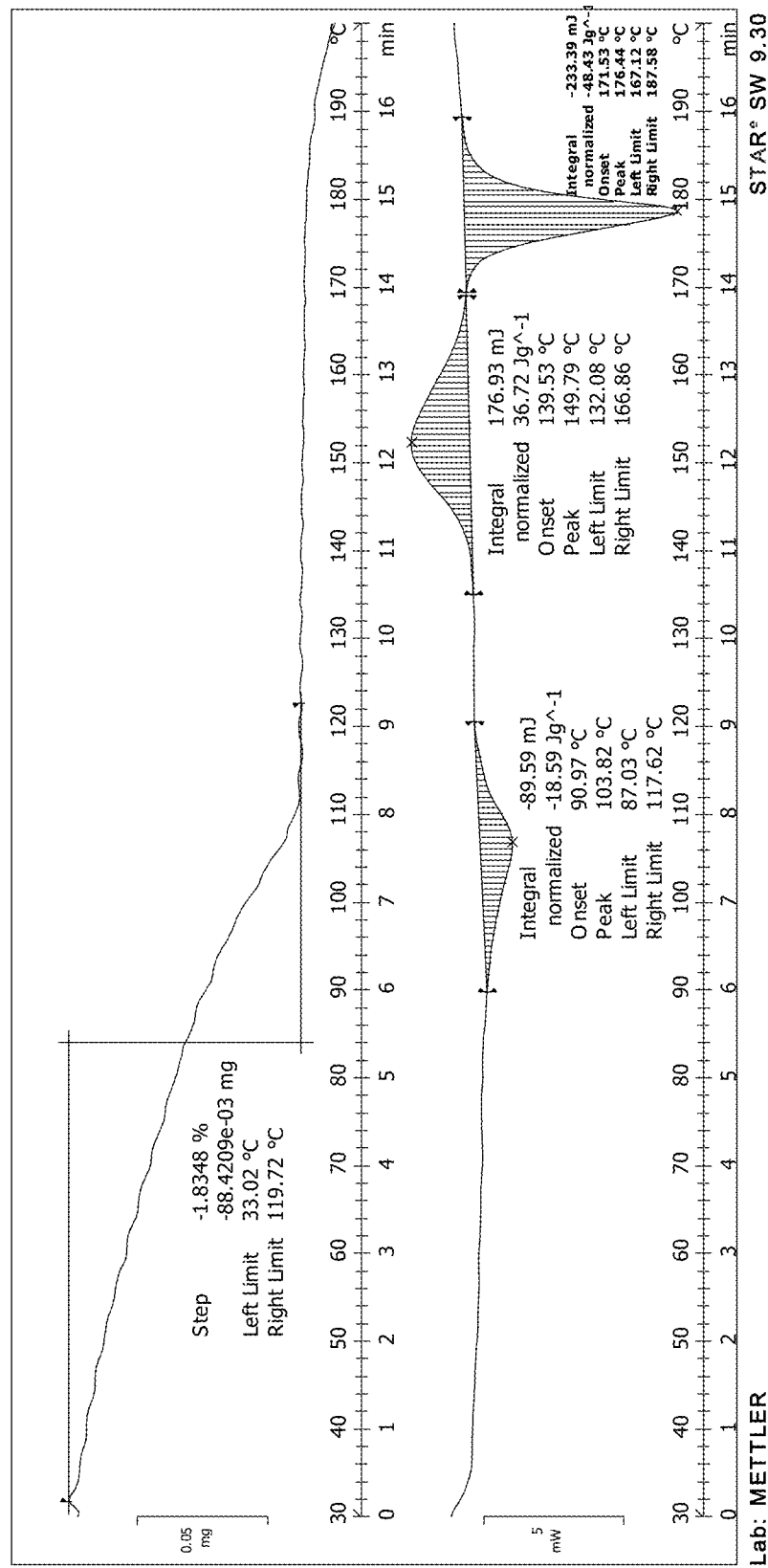
FIG. 2 is a differential scanning calorimetry and thermogravimetric analysis (DSC-TGA) of the crystalline form II of compound 1.
Figure 3:
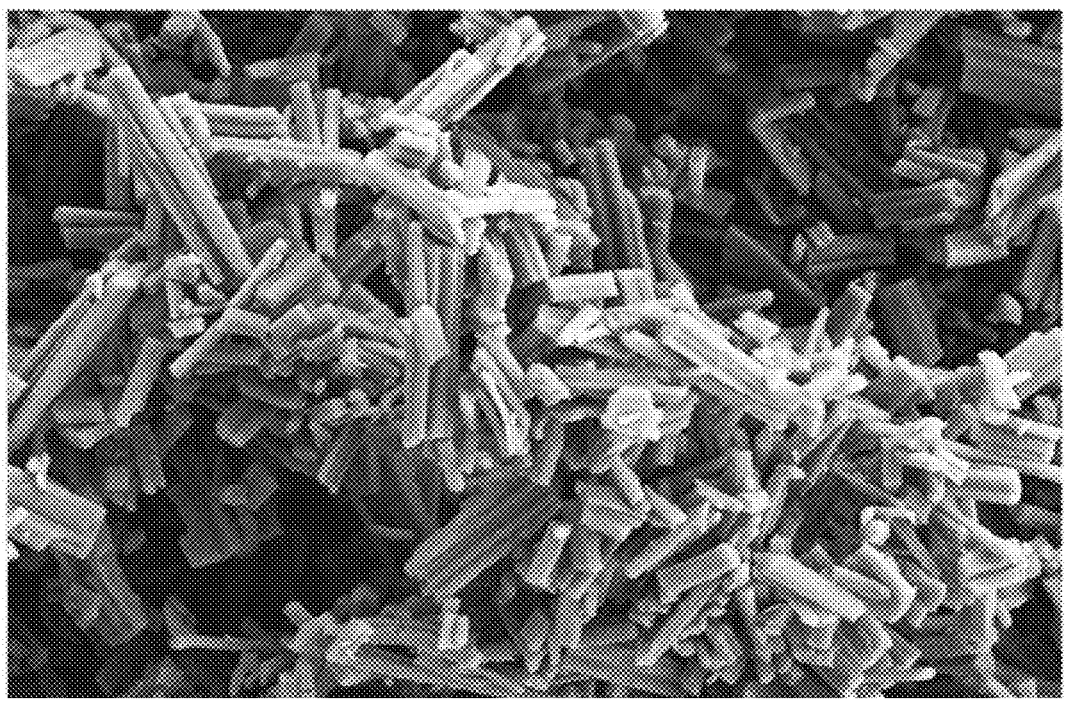
FIG. 3 is a scanning electron micrograph of the crystalline form II of compound 1.

10 g compound 1 was added to 100 mL of dichloromethane, added with 5 mL water, stirred, and heated to reflux. After the solid was completely dissolved, the mixture was cooled to 0° C.-10° C. to precipitate a solid, and the collected solid was the target crystalline form. By X-ray powder diffraction detection, the XRPD pattern thereof was shown in FIG. 1. The DSC-TGA spectrum was shown in FIG. 2 by DSC-TGA analysis. The sample was viewed under a scanning electron microscope, to show its crystal morphology as shown in FIG. 3. The purity of the sample was 99.6%.

Example 3 Preparation of the Crystalline Form II of Compound 1

10 g compound 1 was added to 200 mL dichloromethane, stirred to completely dissolve, added with 7.5 ml water, and continuously stirred to gradually volatilize the solvent to precipitate a solid, and the suspension was filtered to obtain a crystalline form, of which the XRPD pattern was shown in FIG. 1 and the purity was 99.3%.

Example 4 Preparation of the Crystalline Form IV of Compound 1

Figure 6:
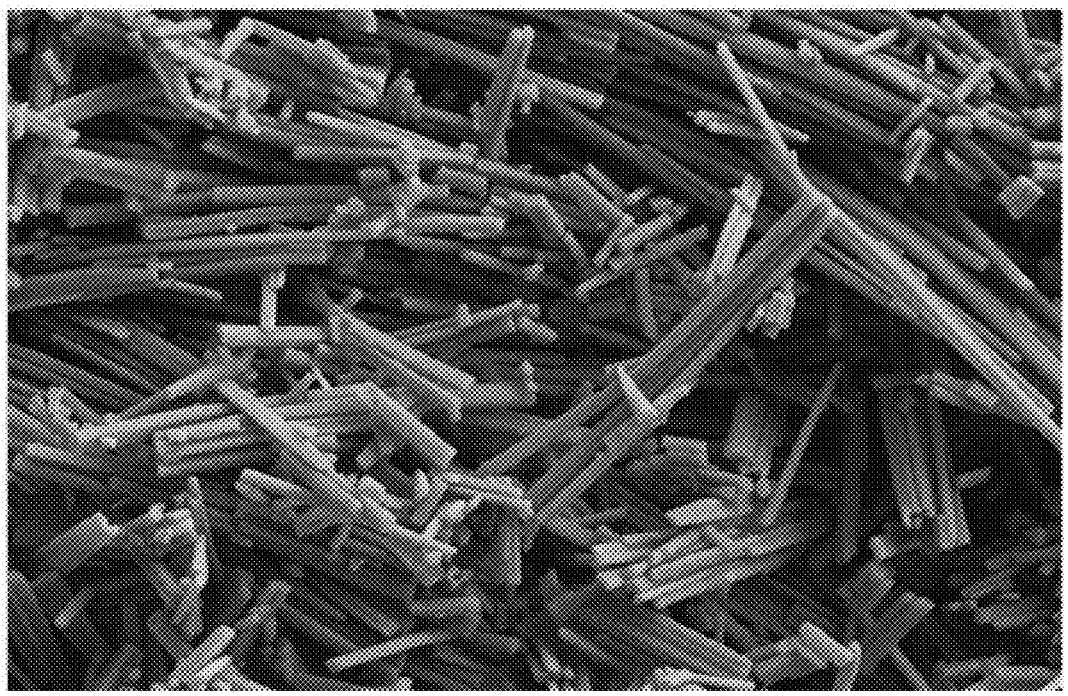
FIG. 6 is a scanning electron micrograph of the crystalline form IV of compound 1.

About 2.3 g compound 1 was added to 10 mL tetrahydrofuran, and the sample was completely dissolved by shaking. The tetrahydrofuran solution was added in one portion to 4.0 mL water and stirred for two hours. The solid obtained by centrifugation was detected by X-ray powder diffraction, of which the XRPD pattern was shown in FIG. 4. The DSC-TGA spectrum thereof was analyzed by DSC-TGA, and the sample was viewed under a scanning electron microscope to show its crystal morphology as shown in FIG. 6, with a purity of 99.1%.

Example 5 Preparation of the Crystalline Form IV of Compound 1

About 2.0 g compound 1 sample was added to 10 mL acetonitrile and the sample was completely dissolved by shaking. The acetonitrile solution was added in one portion to 2.5 mL water and stirred for two hours. The crystalline form was obtained by centrifugation, and its XRPD pattern was shown in FIG. 4, with a purity of 99.5%.

Example 6 Preparation of the Crystalline Form V of Compound 1

1.0 g compound 1 was added to a 10 mL mixed solvent of 1,4-dioxane/n-heptane (1:4; v/v), and the resulting suspension was magnetically stirred at room temperature for 1 day, and then centrifuged to obtain a solid. By X-ray powder diffraction detection, XRPD pattern thereof was shown in FIG. 7, and by DSC-TGA analysis, DSC-TGA spectrum thereof was shown in FIG. 8. The purity thereof was 99.1%.

Example 7 Preparation of the Crystalline Form V of Compound 1

Figure 7:
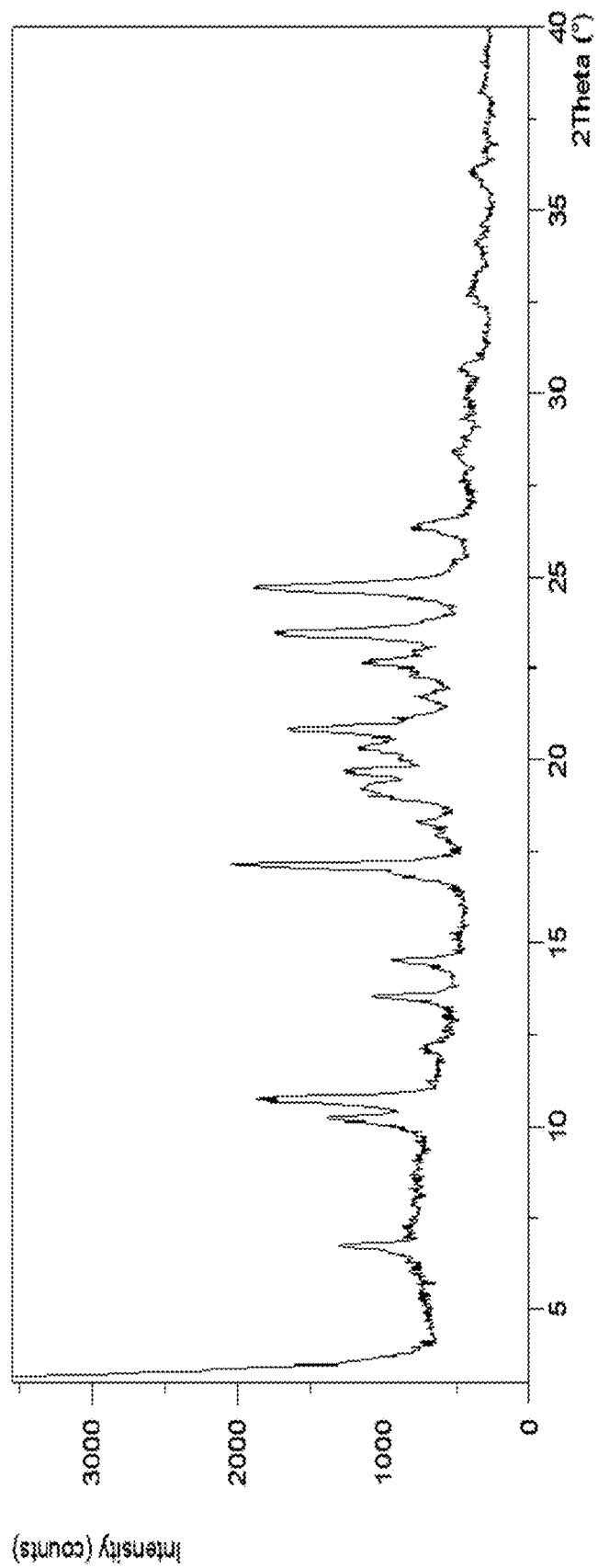
FIG. 7 is an X-ray powder diffraction pattern of the crystalline form V of compound 1.
Figure 8:
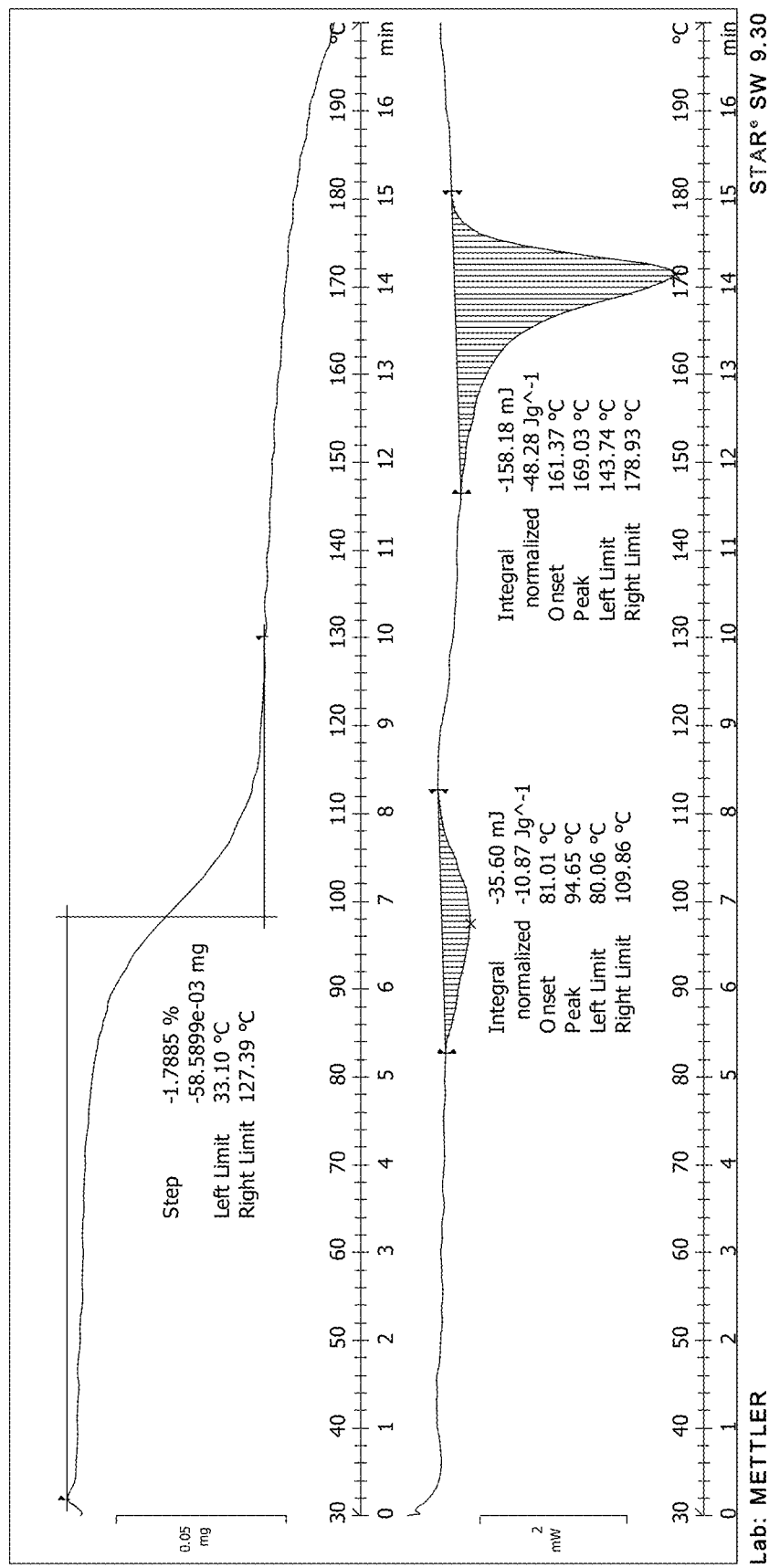
FIG. 8 is a differential scanning calorimetry and thermogravimetric analysis of the crystalline form V of compound 1.

About 1.0 g compound 1 was added to a 8 mL mixed solvent of 1,4-dioxane/n-heptane (1:3; v/v), and the resulting suspension was magnetically stirred at room temperature for 1 day, and then centrifuged to obtain a solid, of which the XRPD pattern was shown in FIG. 7, and the purity was 99.4%.

Example 8 Preparation of the Crystalline Form VI of Compound 1

Figure 10:
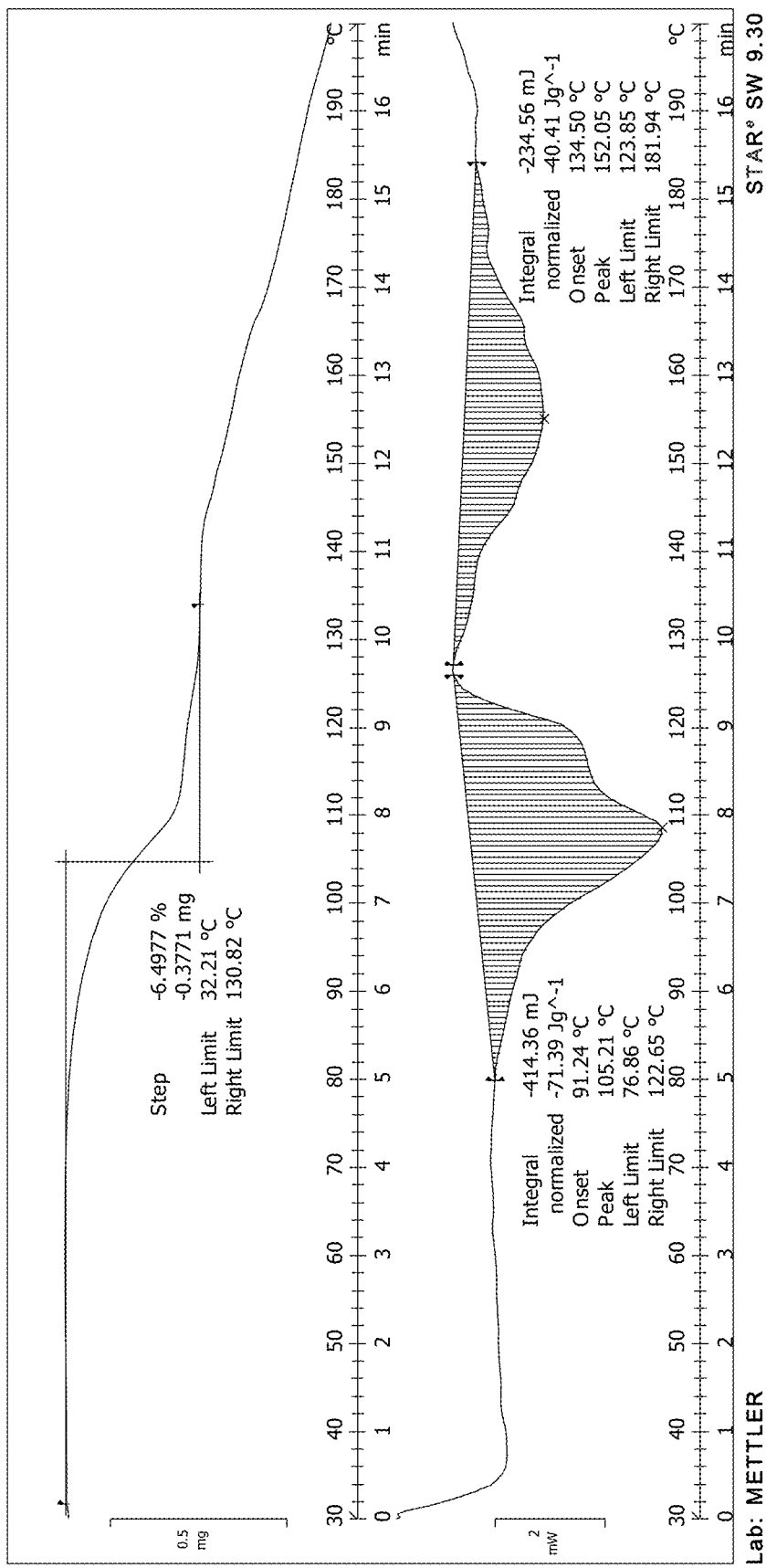
FIG. 10 is a differential scanning calorimetry and thermogravimetric analysis of the crystalline form VI of compound 1.
Figure 11:
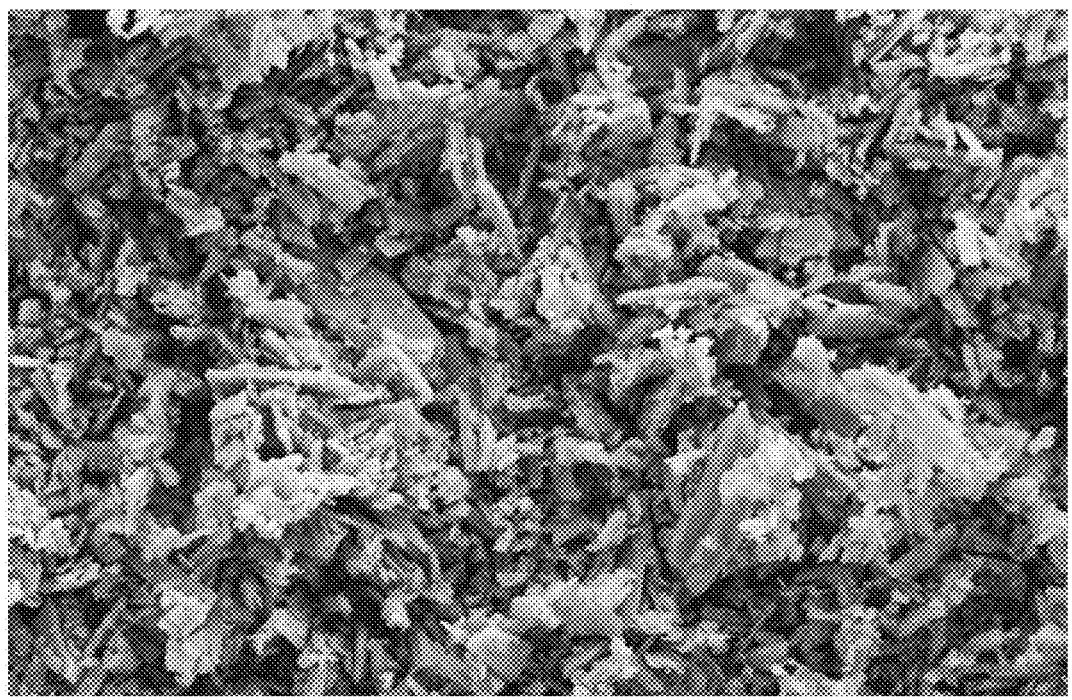
FIG. 11 is a scanning electron micrograph of the crystalline form VI of compound 1.

About 1.3 g compound 1 was added to 5 mL 1,4-dioxane to give a clear solution. To the clear solution, 30 mL n-heptane was added dropwise while being shaked, and magnetically stirred for 3 hours, followed by centrifugation to obtain a solid. By X-ray powder diffraction detection, the XRPD pattern thereof was shown in FIG. 9, and by DSC-TGA analysis, the DSC-TGA spectrum thereof was shown in FIG. 10. The sample was viewed under a scanning electron microscope to show its crystal morphology as shown in FIG. 11. The purity thereof was 99.7%.

Example 9 Preparation of the Crystalline Form VI of Compound 1

About 2.5 g compound 1 was added to 12.5 mL 1,4-dioxane, stirred to obtain a clear solution, and added with 100 mL n-heptane dropwise while stirred, and the obtained suspension solution was magnetically stirred at 50° C. overnight. The solid crystalline form was collected, of which the XRPD pattern was shown in FIG. 9, and the purity was 99.5%.

Example 10 Preparation of the Crystalline Form VII of Compound 1

Figure 13:
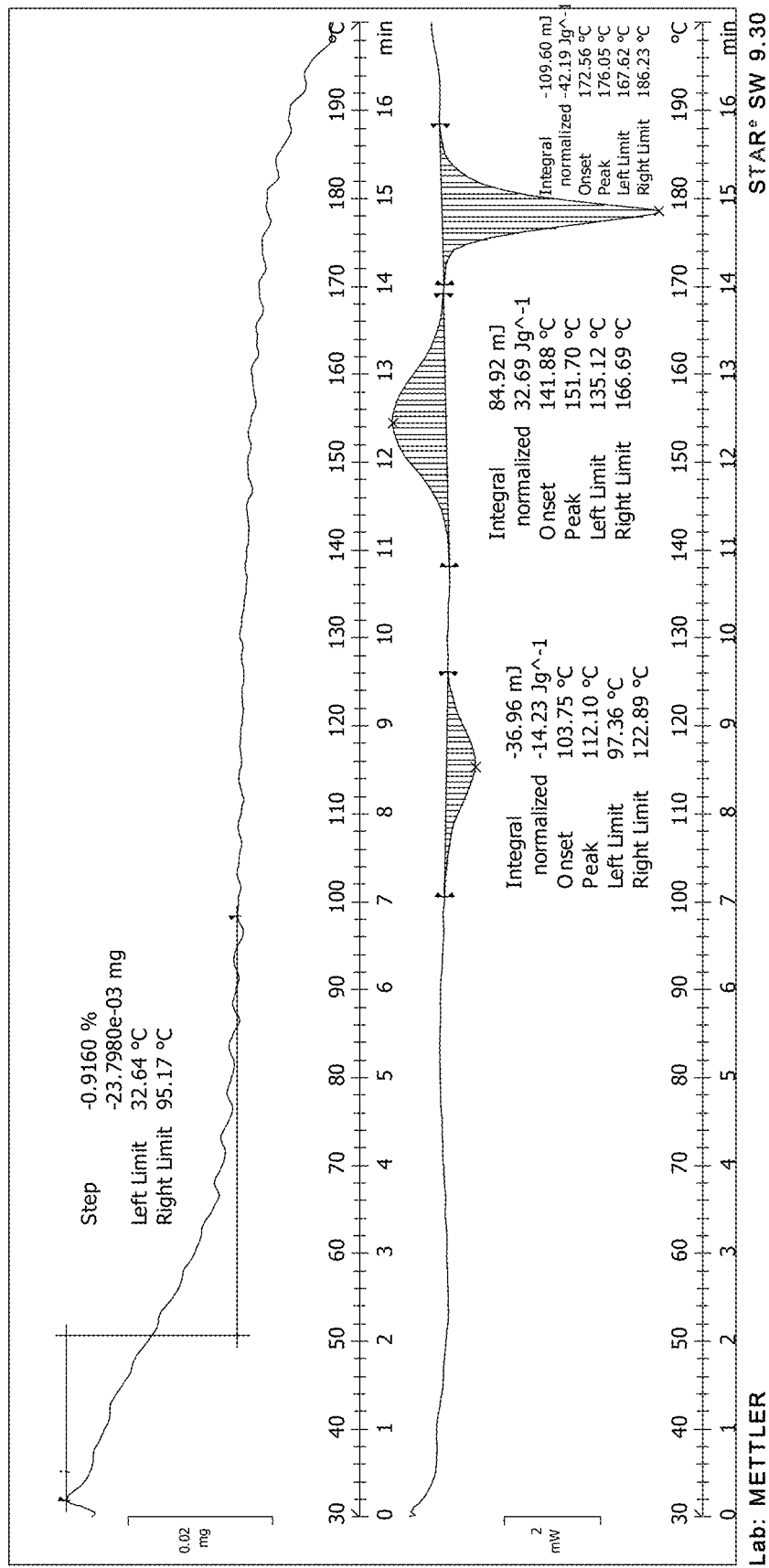
FIG. 13 is a differential scanning calorimetry and thermogravimetric analysis of the crystalline form VII of compound 1.
Figure 14:
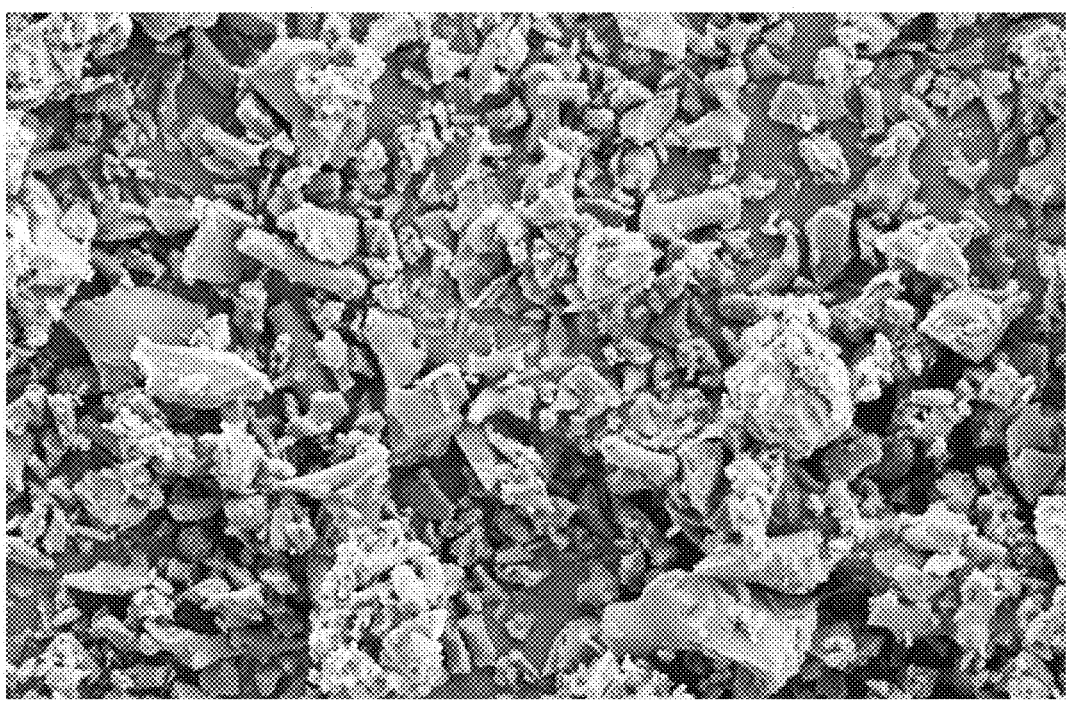
FIG. 14 is a scanning electron micrograph of the crystalline form VII of compound 1.

1.2 g sample of the crystalline form VII of compound 1 was heated to 105° C. under a nitrogen atmosphere, maintained at the temperature for 30 minutes, and then cooled to room temperature to obtain a solid. By X-ray powder diffraction analysis, the XRPD pattern thereof was shown in FIG. 12, and by DSC-TGA analysis, the DSC-TGA spectrum thereof was shown in FIG. 13. The sample was viewed under a scanning electron microscope to show its crystal morphology as shown in FIG. 14, with a purity of 99.6%.

Example 11 Preparation of the Crystalline Form VII of Compound 1

Figure 12:
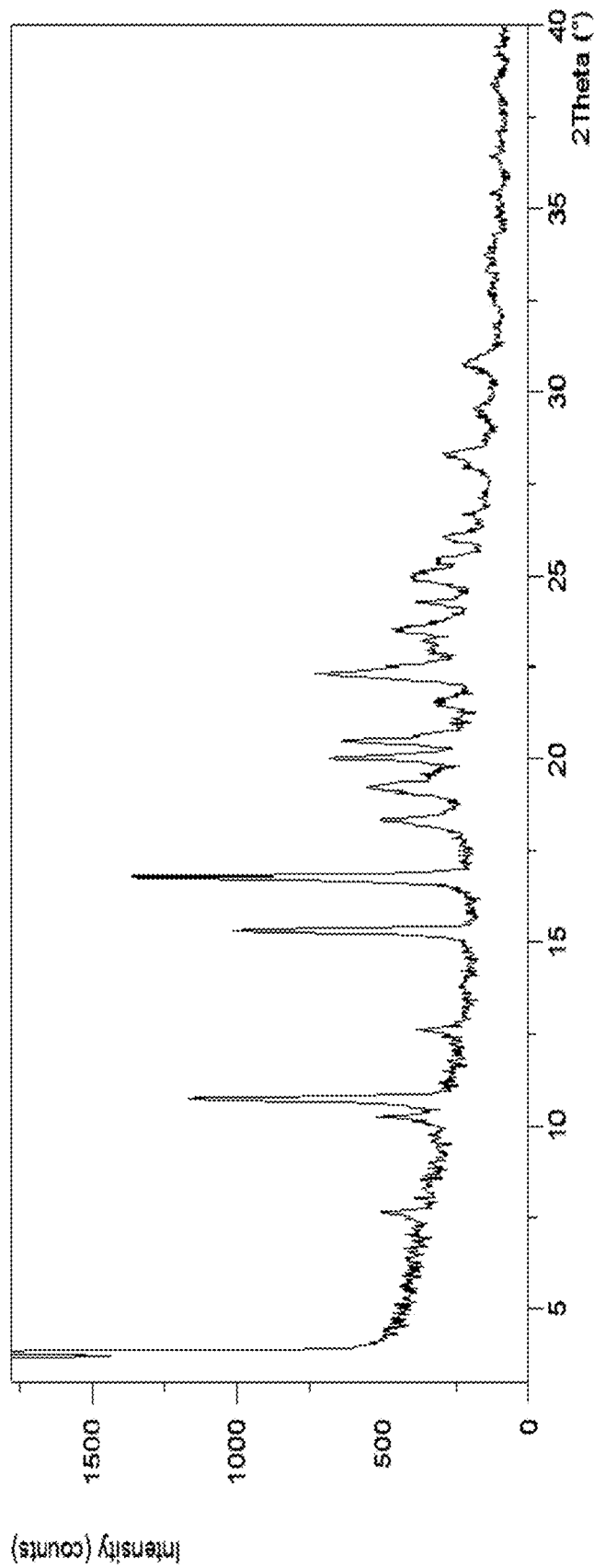
FIG. 12 is an X-ray powder diffraction pattern of the crystalline form VII of compound 1.

1.5 g sample of the crystalline form VII of compound 1 was heated to 120° C. under a nitrogen atmosphere, maintained at the temperature for 20 minutes and then cooled to room temperature to give a solid of crystalline form VII. The crystalline form was obtained, with its XRPD pattern as shown in FIG. 12 and its purity of 99.3%.

Example 12 Stability Test at Room Temperature

The crystalline form II prepared in example 2, crystalline form IV prepared in example 4, crystalline form VI prepared in example 8, and crystalline form VII prepared in example 10 were respectively placed in medicinal low density polyethylene bags, sealed, and maintained at room temperature for 180 days, detected by PANalytical X-ray powder diffractometer for its XRPD, and by high performance liquid chromatography for its purity. The results showed that the purity and crystalline form II, crystalline form IV, crystalline form VI and crystalline form VII of the samples remained unchanged after 180 days, with excellent stability, as shown in Table 6.

TABLE 6

Results of stability test at room temperature

| After 180 days | Crystalline form | Purity |
| --- | --- | --- |
| Crystalline form II | unchanged | 99.5% |
| Crystalline form IV | unchanged | 99.3% |
| Crystalline form VI | unchanged | 99.7% |
| Crystalline form VII | unchanged | 99.5% |

Example 13 Stability Test at High Temperature

The crystalline form II prepared in example 2 was subjected to a stability test at 60° C., and the results were shown in Table 7 below.

TABLE 7

Results of stability test at high temperature

| Initial sample | condition | HPLC purity (%) | | Crystalline form | |
| --- | --- | --- | --- | --- | --- |
| | | Initial | After 10 days | Initial | After 10 days |
| Crystalline form II | 60° C. | 96.8 | 96.6 | Crystalline form II | Crystalline form II |

From the results of Table 7, it was found that the crystalline form II had good stability, and there was no change in purity and crystalline form after 10 days of investigation under high temperature condition.

Example 14 Stability Test Under High Humidity

The crystalline form IV prepared in example 4 was subjected to a stability test at 92.5% RH, and the results were shown in Table 8 below.

TABLE 8

Results of stability test under high humidity

| Initial sample | Condition | HPLC purity (%) | | Crystalline form | |
| --- | --- | --- | --- | --- | --- |
| | | Initial | After 10 days | Initial | After 10 days |
| Crystalline form IV | 92.5% RH | 99.2 | 99.1 | Crystalline form IV | Crystalline form IV |

From the results of Table 8, it was found that the crystalline form IV had good stability, and there was no change in purity and crystal form after 10 days of investigation under high humidity condition.

The embodiments of the present disclosure have been exemplarily described above. However, the present disclosure is not limited to the above embodiment. Any modifications, equivalent substitutions, improvements and the like made within the spirit and scope of the present disclosure are intended to be included within the scope of the present disclosure.

What is claimed is:

1. Crystalline form II of a hemihydrate of compound 1:

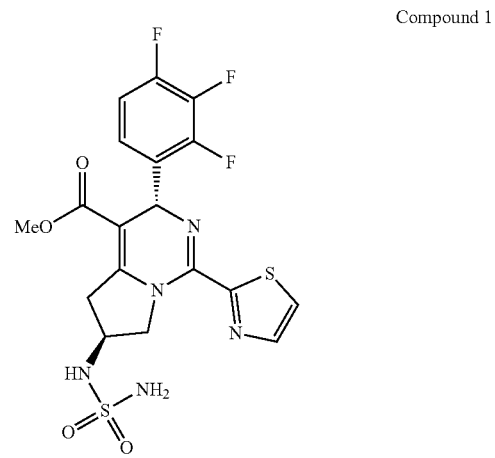 [SMILES: COC(=O)C1=C2C[C@H](NS(N)(=O)=O)CN2C(c2nccs2)=N[C@H]1c1ccc(F)c(F)c1F]

Compound 1 wherein, the crystalline form II is characterized by an X-ray powder diffraction pattern having characteristic peaks at 2θ angles of 4.15±0.20°, 4.99±0.20°, 8.78±0.20°, 9.44±0.20°, 18.47±0.20°, 18.93±0.20° using Cu-Kα radiation.

2. Crystalline form IV of a monohydrate of compound 1:

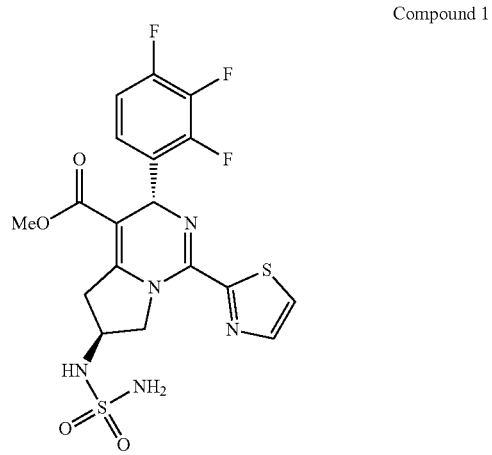 [SMILES: COC(=O)C1=C2C[C@H](NS(N)(=O)=O)CN2C(c2nccs2)=N[C@H]1c1ccc(F)c(F)c1F]

Compound 1 wherein, the crystalline form IV is characterized by an X-ray powder diffraction pattern having characteristic peaks at 2θ angles of 5.04±0.20°, 7.20±0.20°, 7.68±0.20°, 9.81±0.20°, 10.08±0.20°, 14.43±0.20° using Cu-Kα radiation.

3. Crystalline form V of a hemihydrate of compound 1:

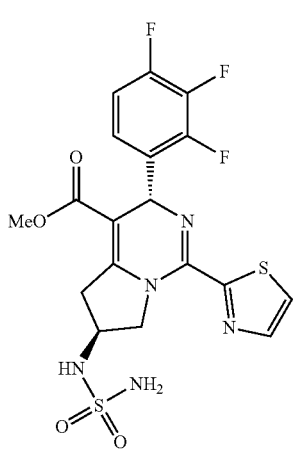
Compound 1 wherein, the crystalline form V is characterized by an X-ray powder diffraction pattern having characteristic peaks at 2θ angles of 6.76±0.20°, 10.20±0.20°, 10.79±0.20°, 17.14±0.20°, 19.26±0.20°, 19.69±0.20°, 20.33±0.20°, 20.83±0.20°, 22.60±0.20°, 23.47±0.20°, 24.73±0.20° using Cu-Kα radiation.

4. Crystalline form VI of a 1,4-dioxane solvate of compound 1:

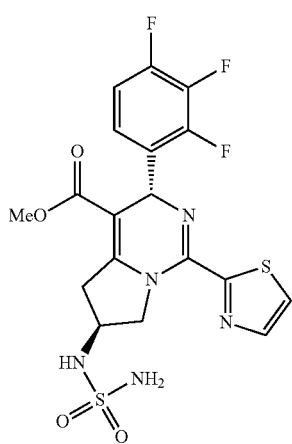
Compound 1 wherein, the crystalline form VI is characterized by an X-ray powder diffraction pattern having characteristic peaks at 2θ angles of 7.82±0.20°, 17.55±0.20°, 19.89±0.20°, 25.48±0.20° using Cu-Kα radiation.

5. Crystalline form VII of an anhydrate of compound 1:

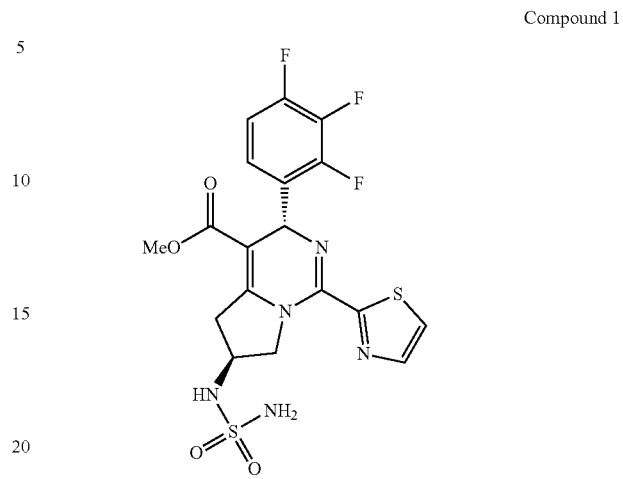
Compound 1 wherein, the crystalline form VII is characterized by an X-ray powder diffraction pattern having characteristic peaks at 2θ angles of 4.94±0.20°, 7.21±0.20°, 7.65±0.20°, 9.85±0.20°, 20.05±0.20°, 23.95±0.20° using Cu-Kα radiation.

6. The crystalline form II according to claim 1, having an X-ray powder diffraction pattern having characteristic peaks at 2θ angles of 4.15±0.20°, 4.99±0.20°, 7.33±0.20°, 8.78±0.20°, 9.44±0.20°, 10.00±0.20°, 18.47±0.20°, 18.93±0.20° using Cu-Kα radiation.

7. The crystalline form II according to claim 1, having an X-ray powder diffraction pattern substantially as shown in FIG. 1.

8. The crystalline form IV according to claim 2, having an X-ray powder diffraction pattern having characteristic peaks at 2θ angles of 5.04±0.20°, 7.20 ±0.20°, 7.68±0.20°, 9.35 ±0.20°, 9.81±0.20°, 10.08±0.20°, 14.43±0.20, 18.07±0.20° using Cu-Kα radiation.

Figure 4:
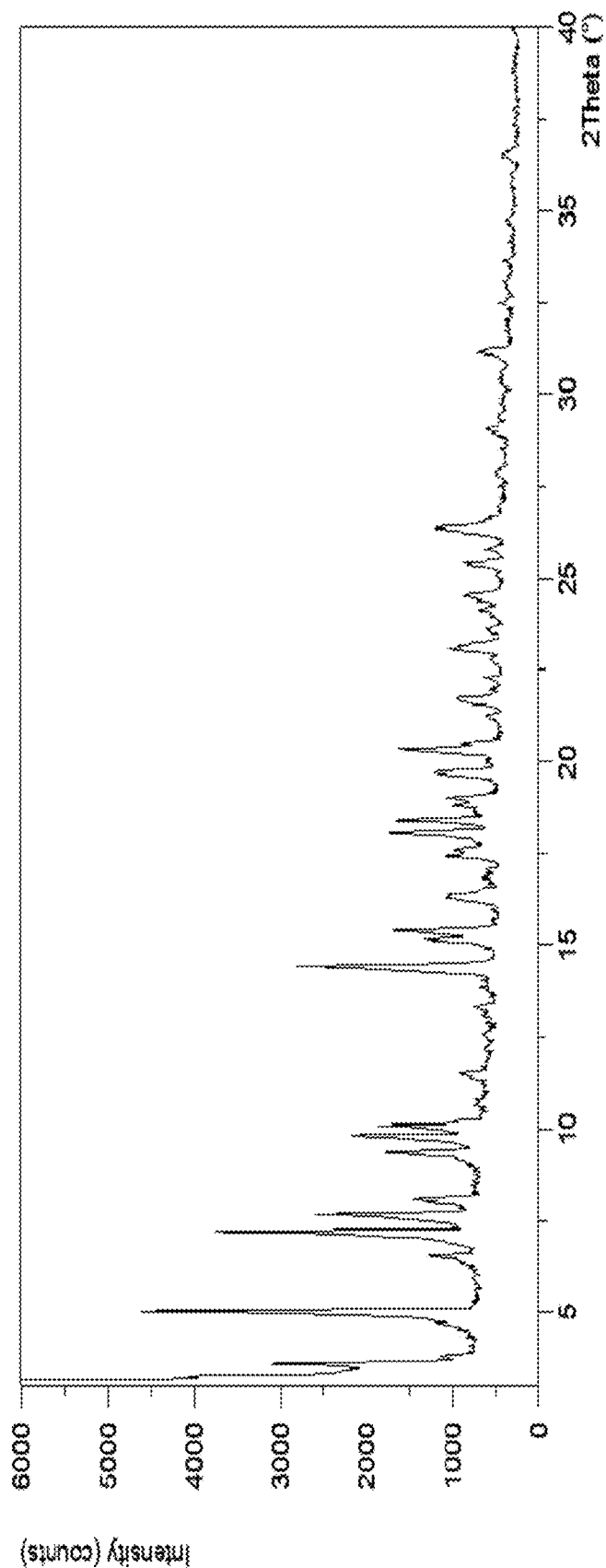
FIG. 4 is an X-ray powder diffraction pattern of the crystalline form IV of compound 1.
Figure 5:
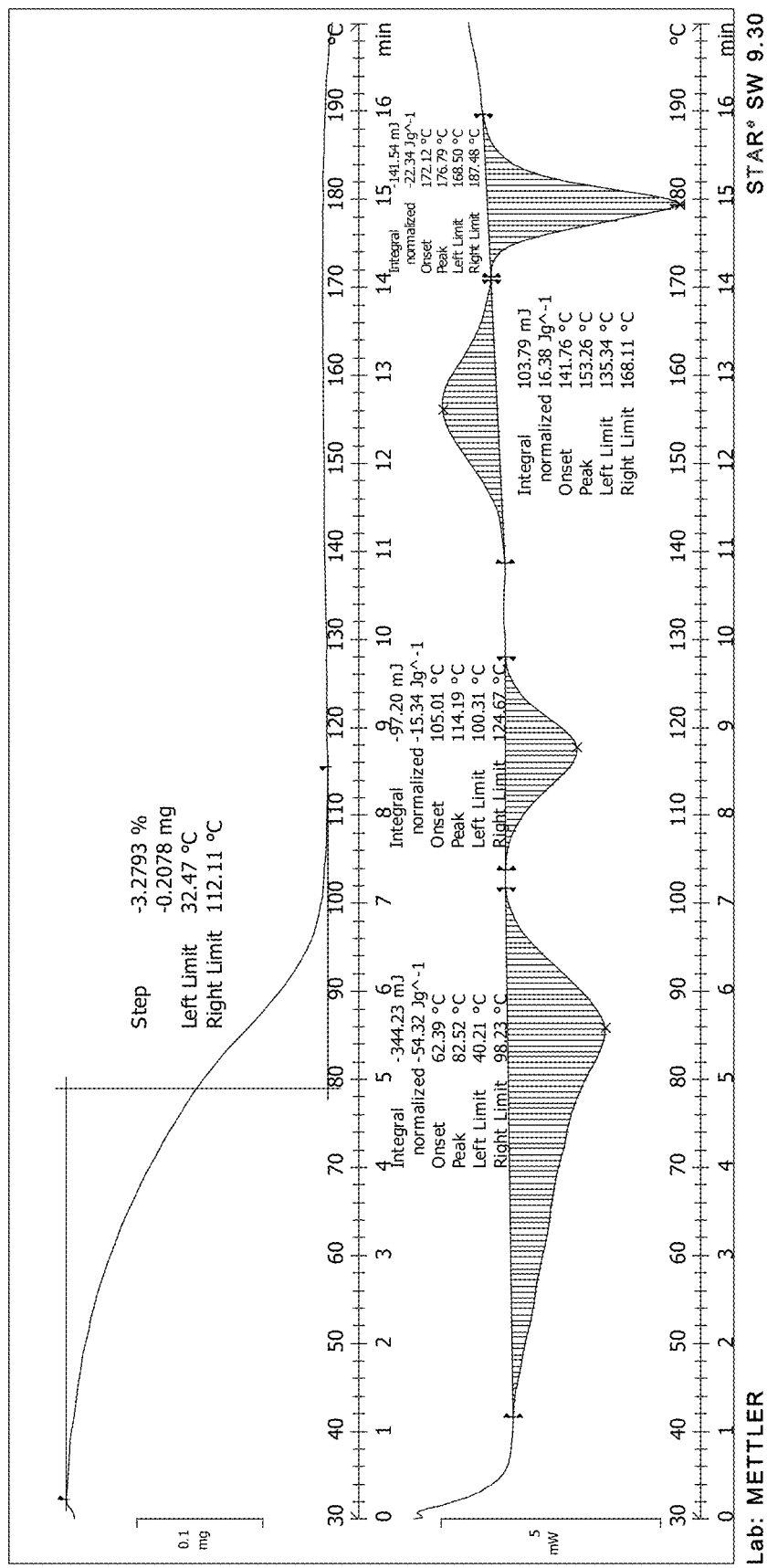
FIG. 5 is a differential scanning calorimetry and thermogravimetric analysis of the crystalline form IV of compound 1.

9. The crystalline form IV according to claim 2, having an X-ray powder diffraction pattern substantially as shown in FIG. 4.

10. The crystalline form V according to claim 3, having an X-ray powder diffraction pattern substantially as shown in FIG. 7.

11. The crystalline form VI according to claim 4, having an X-ray powder diffraction pattern having characteristic peaks at 2θ angles of 5.57±0.20°, 7.82±0.20°, 12.30±0.20°, 17.55±0.20°, 18.34±0.20°, 19.15±0.20°, 19.89±0.20°, 24.46±0.20°, 25.48±0.20° using Cu-Kα radiation.

Figure 9:
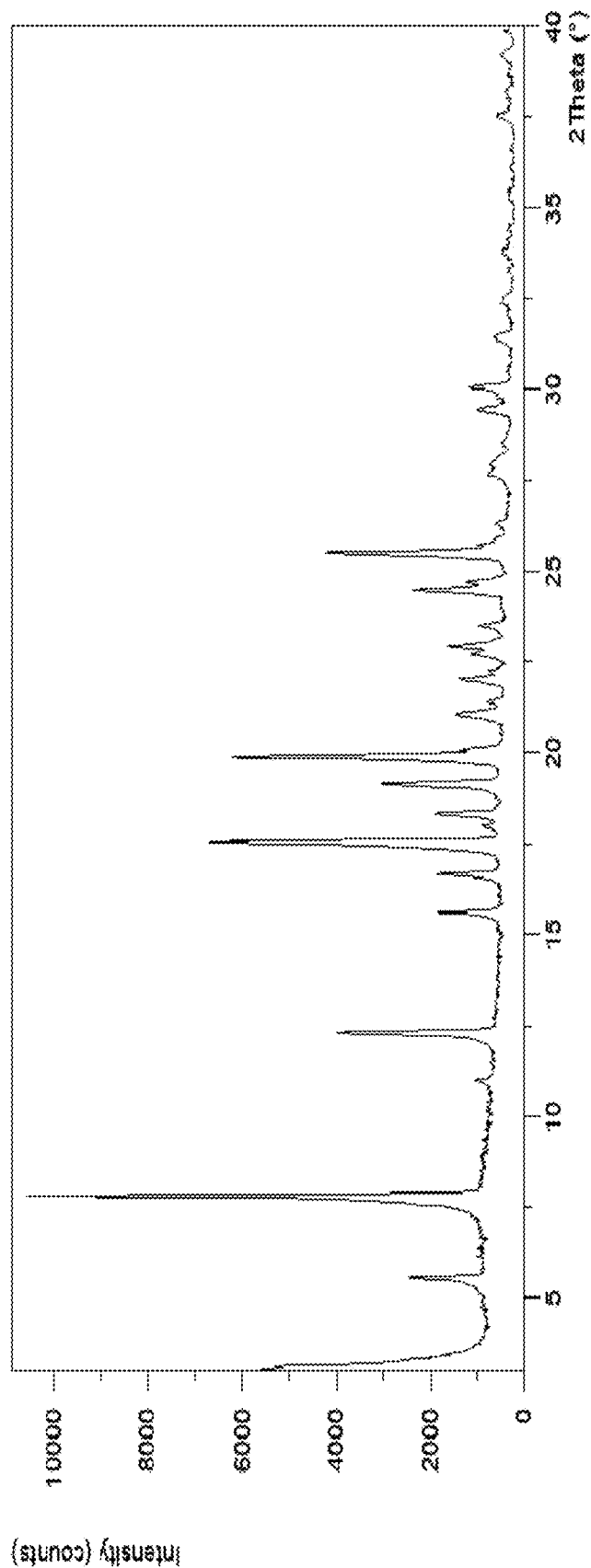
FIG. 9 is an X-ray powder diffraction pattern of the crystalline form VI of compound 1.

12. The crystalline form VI according to claim 4, having an X-ray powder diffraction pattern substantially as shown in FIG. 9.

13. The crystalline form VII according to claim 5, having an X-ray powder diffraction pattern having characteristic peaks at 2θ angles of 4.94±0.20°, 7.21±0.20°, 7.65±0.20°, 8.01 ±0.20°, 9.85±0.20°, 14.54±0.20°, 20.05±0.20°, 23.95±0.20° using Cu-Kα radiation.

14. The crystalline form VII according to claim 5, having an X-ray powder diffraction pattern having characteristic peaks at 2θ angles of 4.94±0.20°, 7.21±0.20°, 7.65±0.20°, 8.01 ±0.20°, 9.85±0.20°, 14.54±0.20°, 16.21±0.20°, 17.64±0.20°, 18.28±0.20°, 18.65±0.20°, 20.05±0.20°, 22.59±0.20°, 23.95±0.20° using Cu-Kα radiation.

15. The crystalline form VII according to claim 5 having an X-ray powder diffraction pattern substantially as shown in FIG. 12.

16. A preparation method of the crystalline form II according to claim 1, comprising:
  mixing the compound 1 with a halogenated alkane solvent to obtain a solution, adding water to the solution form a solvent, and volatilizing or evaporating the solvent to obtain the crystalline form II,
  wherein the halogenated alkane solvent is selected from one or more of the group consisting of dichloromethane, chloroform, and carbon tetrachloride,
  wherein a mass (g)-to-volume (mL) ratio of compound 1 to the halogenated alkane solvent ranges from 1:2 to 1:50,
  wherein a volume ratio of the halogenated alkane solvent to water ranges from 1:1 to 40:1; and
  the volatilization is carried out at a temperature suitable for volatilization or evaporation of the solvent.

17. A preparation method of the crystalline form IV according to claim 2, comprising:
  dissolving the compound 1 in an ether solvent or a nitrile solvent, adding the resulting solution to water, and stirring at 0-40° C. to obtain the crystalline form IV,
  wherein the ether solvent is selected from the group consisting of diethyl ether, methyl ethyl ether, methyl tert-butyl ether, dipropyl ether, dibutyl ether, 1,4-dioxane, tetrahydrofuran, and mixtures thereof, and the nitrile solvent is acetonitrile,
  wherein a mass (g)-to-volume(mL) ratio of the compound 1 to the ether solvent or the nitrile solvent ranges from 1:2 to 1:50, and
  wherein a volume ratio of the ether or nitrile solvent to the water ranges from 2:1 to 4:1.

18. A preparation method of the crystalline form V according to claim 3, comprising:
  dissolving the compound 1 in a mixed solvent containing an ether solvent and an alkane solvent to obtain a suspension, stirring at 0-40° C. to crystallize to obtain the crystalline form V,
  wherein the ether solvent is selected from one or more of the group consisting of diethyl ether, methyl ethyl ether, methyl tert-butyl ether, dipropyl ether, dibutyl ether, 1,4-dioxane, and tetrahydrofuran, and mixtures thereof, and the alkane solvent is a $C_{6-10}$ linear or branched alkane,
  wherein, in the mixed solvent, a volume ratio of the ether solvent to the alkane solvent ranges from 1:1 to 1:4, and
  wherein a mass (g)-to-volume (mL) ratio of the compound 1 to the mixed solvent ranges from 1:5 to 1:100.

19. A preparation method of the crystalline form VI according to claim 4, comprising:
  dissolving the compound 1 in a solvent of 1,4-dioxane to obtain a solution, adding an alkane solvent to the solution, and stirring at 0-60° C. to obtain the crystal form VI,
  wherein the alkane solvent is a $C_{6-10}$ linear or branched alkane,
  wherein a mass (g)-to-volume (mL) ratio of the compound 1 to 1,4-dioxane ranges from 1:2 to 1:50, and
  wherein a volume ratio of the 1,4-dioxane to the alkane solvent ranges from 1:4 to 1:8.

20. A preparation method of the crystalline form VII according to claim 5, comprising:
  heating the crystalline form IV of a monohydrate of compound 1 at 100-150° C. for 5-50 minutes under an inert atmosphere,
  wherein the crystalline form IV has an X-ray powder diffraction pattern having characteristic peaks at 2θ angles of 5.04±0.20°, 7.20±0.20°, 7.68±0.20°, 9.81±0.20°, 10.08±0.20°, 14.43±0.20° using Cu-Kα radiation;
  and cooling to obtain the crystalline form VII.

* * * * *